(12) United States Patent
Sinko et al.

(10) Patent No.: US 9,345,662 B2
(45) Date of Patent: May 24, 2016

(54) DEGRADABLE HYDROGEL COMPOSITIONS AND METHODS

(75) Inventors: Patrick J. Sinko, Annandale, NJ (US); Manjeet Deshmukh, Edison, NJ (US); Yashveer Singh, Highland Park, NJ (US); Simi Gunaseelan, North Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 1031 days.

(21) Appl. No.: 13/129,949

(22) PCT Filed: Nov. 20, 2009

(86) PCT No.: PCT/US2009/065225
§ 371 (c)(1),
(2), (4) Date: Aug. 4, 2011

(87) PCT Pub. No.: WO2010/059883
PCT Pub. Date: May 27, 2010

(65) Prior Publication Data
US 2011/0286926 A1    Nov. 24, 2011

Related U.S. Application Data

(60) Provisional application No. 61/115,962, filed on Nov. 19, 2008.

(51) Int. Cl.
| | |
|---|---|
| *A61K 47/06* | (2006.01) |
| *A61K 9/00* | (2006.01) |
| *A61K 47/48* | (2006.01) |
| *A61K 49/00* | (2006.01) |
| *A61K 9/06* | (2006.01) |

(52) U.S. Cl.
CPC ......... *A61K 9/0024* (2013.01); *A61K 47/48215* (2013.01); *A61K 47/48784* (2013.01); *A61K 49/0032* (2013.01); *A61K 49/0041* (2013.01); *A61K 49/0043* (2013.01); *A61K 49/0073* (2013.01); *A61K 9/06* (2013.01)

(58) Field of Classification Search
CPC .................. A61K 47/48784; A61K 49/0073
USPC .................................... 424/400, 457; 562/573
See application file for complete search history.

(56) References Cited

U.S. PATENT DOCUMENTS

| | | | |
|---|---|---|---|
| 5,066,490 A | 11/1991 | Neville, Jr. et al. | |
| 2004/0214783 A1 | 10/2004 | Terman | |
| 2005/0119762 A1* | 6/2005 | Zilla et al. ................. | 623/23.75 |
| 2005/0208095 A1 | 9/2005 | Hunter et al. | |
| 2005/0282747 A1* | 12/2005 | Clark et al. ..................... | 514/12 |
| 2006/0002890 A1 | 1/2006 | Hersel et al. | |
| 2007/0092906 A1* | 4/2007 | Murphy et al. .................. | 435/6 |
| 2007/0128681 A1 | 6/2007 | Barman et al. | |
| 2007/0191366 A1 | 8/2007 | Hoffmann et al. | |
| 2010/0196439 A1* | 8/2010 | Beck et al. .................... | 424/424 |

FOREIGN PATENT DOCUMENTS

| | | |
|---|---|---|
| WO | 2006/069344 | 6/2006 |
| WO | 2008/060552 | 5/2008 |

OTHER PUBLICATIONS

Lutolf M. P. (Biomacromolecules 4:713-22, 2003).*

* cited by examiner

*Primary Examiner* — David Lukton
(74) *Attorney, Agent, or Firm* — Fox Rothschild LLP

(57) ABSTRACT

This invention concerns an in situ biodegradable hydrogel drug delivery system in which the components are assembled in a manner that provides a mechanism for the timed cleavage of a particular amide bond in a covalently linked active agent or of the hydrogel structure.

19 Claims, 11 Drawing Sheets

SEQUENCE LISTING

<160> NUMBER OF SEQ ID NOS: 8

<210> SEQ ID NO 1
<211> LENGTH: 11
<212> TYPE: PRT
<213> ORGANISM: Artificial
<220> FEATURE:
<223> OTHER INFORMATION: Synthetic

<400> SEQUENCE: 1

Leu Gly Ala Ser Trp His Arg Pro Asp Lys Cys
1               5                   10

<210> SEQ ID NO 2
<211> LENGTH: 9
<212> TYPE: PRT
<213> ORGANISM: Artificial
<220> FEATURE:
<223> OTHER INFORMATION: Synthetic

<400> SEQUENCE: 2

Cys Gly Asn Lys Arg Thr Arg Gly Cys
1               5

<210> SEQ ID NO 3
<211> LENGTH: 14
<212> TYPE: PRT
<213> ORGANISM: Artificial
<220> FEATURE:
<223> OTHER INFORMATION: Synthetic

<400> SEQUENCE: 3

Gln Cys Arg Pro Ser Lys Gly Arg Lys Arg Gly Phe Cys Trp
1               5                   10

<210> SEQ ID NO 4
<211> LENGTH: 5
<212> TYPE: PRT
<213> ORGANISM: Artificial
<220> FEATURE:
<223> OTHER INFORMATION: Synthetic

<400> SEQUENCE: 4

Glu Leu Gly Leu Gly
1               5

<210> SEQ ID NO 5
<211> LENGTH: 4
<212> TYPE: PRT
<213> ORGANISM: Artificial
<220> FEATURE:
<223> OTHER INFORMATION: Synthetic

<400> SEQUENCE: 5

Arg Gly Asp Cys
1

<210> SEQ ID NO 6
<211> LENGTH: 4
<212> TYPE: PRT
<213> ORGANISM: Artificial
<220> FEATURE:
<223> OTHER INFORMATION: Synthetic

<400> SEQUENCE: 6

Arg Gly Asp Ser
1

```
<210> SEQ ID NO 7
<211> LENGTH: 6
<212> TYPE: PRT
<213> ORGANISM: Artificial
<220> FEATURE:
<223> OTHER INFORMATION: Synthetic

<400> SEQUENCE: 7

Phe Arg Gly Asp Ser Pro
1               5

<210> SEQ ID NO 8
<211> LENGTH: 5
<212> TYPE: PRT
<213> ORGANISM: Artificial
<220> FEATURE:
<223> OTHER INFORMATION: Synthetic

<400> SEQUENCE: 8

Arg Gly Asp Tyr Lys
1               5
```

DEGRADABLE HYDROGEL COMPOSITIONS AND METHODS

CROSS-REFERENCE TO RELATED APPLICATIONS

This application is the 35 U.S.C. §371 National Phase Application of International Application Serial No. PCT/US2009/065225, filed Nov. 20, 2009, which claims priority to provisional application 61/115962, filed Nov. 19, 2008, the disclosures of which are hereby incorporated by reference in its entirety.

BACKGROUND OF THE INVENTION

1. Field of the Invention

This invention concerns an in situ biodegradable hydrogel drug delivery system in which the components are assembled in a manner that provides a mechanism for the timed cleavage of a particular amide bond in a covalently linked active agent, leading to release of that agent, or of a particular amide bond in the hydrogel matrix, leading to the degradation of the hydrogel itself. The present invention utilizes timed bond degradation resulting in hydrogel degradation and/or release of an active agent from the hydrogel. Two mechanisms of agent loading for the hydrogel include: (i) passive entrapment; and (ii) covalent attachment. The present invention incorporates novel hydrogel chemistry enabling a time based biodegradation mechanism for the hydrogel. Thus, after an active agent has been released from the hydrogel, the hydrogel will be degraded via this biodegradation mechanism into smaller, soluble PEG conjugates, which are naturally cleared from the body (renal, hepatic, and so on) without resorting to surgical or other invasive procedures. Although not intended to limit the invention, the hydrogels in the present invention could be preferably used for following: (i) subcutaneous delivery of active agents into the body; and (ii) local intra-ductal delivery of active agents to the breast ducts for the treatment and image-guided interventions in ductal carcinoma in situ (DCIS).

2. Description of the Related Art

Hydrogels are cross-linked network of hydrophilic polymers with ability to absorb large amount of water and swell, while maintaining their three-dimensional structure. The molecules of different sizes can diffuse into and out of this swollen three-dimensional network, which allows their possible use as drug-depot for controlled release applications. Hydrogels show minimum tendency to adsorb protein from body fluids due to their low interfacial tension and they also resemble closely to the living tissue due to their high-water content, and soft and rubbery characteristics. Due to their above-mentioned properties, hydrogels find use as scaffolds in tissue engineering and drug delivery systems in various biomedical and pharmaceutical applications[1,2]. Most hydrogel-based drug delivery systems are implants designed to release drug locally at a predetermined rate.

Hydrogels are prepared by intermolecular crosslinking of polymer chains through multifunctional crosslinkers. Amongst the different polymers available, the poly(ethylene glycol) or PEG polymers are probably the most versatile polymers for medical applications because they possess chemically inert polyether backbone and show excellent solubility in aqueous media. PEG's are nontoxic, non-immunogenic, and non-biodegradable, which makes them suitable for modification with biologically active compounds[3]. Several PEG hydrogels have been prepared using different crosslinking mechanisms for drug delivery applications[4-10]. Unfortunately, the hydrogels when prepared using non-degradable chemical bonds are not cleared from the body unless removed by surgical or other invasive means, which is inconvenient at best. Therefore, biodegradation (chemical or enzymatic cleavage in physiological environment) has become an important criterion for hydrogel drug delivery systems as it ensures that the drug depot is naturally removed from the body by utilizing the existing clearing mechanisms (renal, hepatic, and so on), one the drug delivery objectives have been achieved.

Different degradable or cleavable chemical linkages have been used for conjugating the active agents to PEG's or other polymeric carriers, which includes: (i) autodegradable esters bonds; (ii) acid sensitive linkages like acetals, imines (Schiff bases), cis-aconityls, and hydrazones; (iii) reducible bond like disulfides; and (iv) enzyme-degradable peptide spacers[11]. The polymer such as poly-glutamate (PGA) has been used for conjugation with paclitaxel through degradable ester bond linked to the α-carboxylic moiety of PGA[12]. Henne et al. have synthesized novel folate peptide camptothecin conjugate to release free CPT under reduced conditions using releasable disulfide carbonate linker capable of conferring water solubility to the conjugate[13]. Furthermore, polymer-doxorubicin ("Dox"), conjugates with Schiff base linkages, which release Dox when exposed to acidic conditions, have been obtained[11]. HPMA-Gly-Phe-Leu-Gly-Dox conjugate has been developed in which the in-built tetrapeptidyl linker (Gly-Phe-Leu-Gly) is cleaved by cathepsin B enzyme to release the free dox[14].

Degradable or cleavable bonds like esters, phosphate ester, anhydrides, imine, acetal, and ketal have been incorporated into the hydrogel matrix to obtain biodegradable hydrogel drug delivery systems[15]. Harris and Zhao[4] reported the preparation of degradable hydrogels using, degradable ester bonds. They developed amine-reactive bifunctional PEG crosslinkers containing degradable ester bonds with in the crosslinker structure. They used these crosslinkers for intermolecular crosslinking of branched PEG amines to obtain degradable hydrogels and also showed the covalent attachment of protein to the hydrogel matrix through ester bonds. The release of the protein from the hydrogel was controlled by hydrolysis of ester bonds between the protein (active agent) and the hyrogel matrix (drug depot). Andac et al.[16] prepared biodegradable hydrogels using disulfide-linked components, which could be cleaved with reducing agents. The PEG hydrogels have been degraded naturally by enzymes[17]. Enzymatically degradable hydrogels containing passively entrapped (no covalent bond between the active agent and the carrier) have also been obtained[18]. Another variant known is the polymer drug conjugate covalently linked to the hydrogel matrix through an enzyme cleavable linker[19]. Saito and Hoffman[11] developed polymer-dox conjugates, which could be covalently linked to biodegradable PEG hydrogels using acid cleavable Schiff base linkages.

However, polymeric carriers or hydrogel drug delivery systems developed, using the existing degradation technology do not exhibit timed degradation of the hydrogel matrix or the release of active agents. The present invention aims to fill this existing technology gap by developing PEG hydrogel technology, where the hydrogel biodegradations and the release of active agents from the hydrogel are timed, ("controlled").

SUMMARY OF THE INVENTION

The present disclosure describes: (i) linear and multiarm PEG and other polymers suitable for the preparation of biodegradable hydrogels; (ii) synthesis and characterization of multifunctional PEG crosslinkers for timed biodegradation of hydrogels; (ii) preparation of biodegradable hydrogels with passively entrapped active agents; (iii) biodegradation studies in buffer and plasma; and (iv) covalent attachment of active agents to the hydrogel matrix and their timed release. This disclosure also describes the most preferred use of present invention: (i) depot for subcutaneous release of active agents (mouse model); and (ii) local intraductal delivery of active agents to the breast ducts (rat model) for the treatment and image-guided interventions in ductal carcinoma in situ (DCIS).

The hydrogel is based on intermolecular crosslinking of soluble PEG polymers, which forms an insoluble, high molecular weight PEG hydrogel matrix. Active agents may be loaded into this hydrogel prior to the cross-linking reaction, so that the hydrogel win serve as a depot for the sustained release of that agent. However, when release of drug is complete, the spent hydrogel will remain as a lump under the skin. Rather than surgically removing the spent hydrogel, we have devised a process that can cause the spent hydrogel to degrade at a preselected time, which would be after drug release has been completed. This biodegradation reaction is designed to be independent of any other chemical groups in the hydrogel or in the active agent. Preferably, the chemical reaction used for forming the hydrogel by cross linking should not interfere with the chemical reaction used for biodegradation. Not limiting examples of methods to accomplish this includes: (i) using chemoselective pairs of reactive groups, for example, the cross-linker may comprise a thiol-reactive group such as vinylsulfone or maleimide that will react with thiol groups on PEG; and (ii) using steric effects to favor the crosslinking reaction.

There are many variations, all of which are considered embodiments of the invention, in the general scheme for hydrogel preparation. One such embodiment as shown in the FIG. 1 uses multi-arm thiol-containing PEG with bifunctional PEG crosslinker containing vinylsulfone or maleimide groups. Upon mixing the multi-arm PEG with the bifunctional crosslinker under proper conditions of pH, reagent concentrations and temperature, covalent bonds are formed due to the reaction of the thiol group with the vinylsulfone or maleimide groups. The transition from a liquid to a hydrogel will occur when the network of intermolecularly crosslinked PEG molecules reaches a particular molecular weight, which depends on many factors. In this embodiment, the cross-linker contains both the chemoselective group needed for hydrogel formation and a separate chemical group needed for the biodegradation reaction. The present invention is directed in part, to materials and methods for the preparation and use of hydrogels incorporating chemistries allowing for timed degradation and/or release of active agents, which may be embedded therein by covalent or non-covalent means.

This new self-cleaving mechanism of the cross-linker is based on a chemical reaction in which an N-terminal residue of glutamine in a peptide participates in the displacement of its γ-amino group by its α-amino group (FIG. 2). As a result, the glutamine residue becomes the cyclic analog, pyro-glutamic acid, and one equivalent of ammonia is released (FIG. 2). An example of this spontaneous reaction is the pituitary hormone, luteinizing hormone releasing hormone (LHRH)[20]. We sought to utilize this mechanism for the controlled degradation of a hydrogel. In this similar but new mechanism, an amino compound would be attached to the γ-carboxyl group and the leaving group would be a primary amino compound rather than ammonia. (FIG. 3). The validity of our hypothesis was confirmed using Glutathione (GSH), as a model to study the time dependent self-elimination mechanism. Systematic non-enzymatic degradation of GSH at pathological (pH=6.2, 6.8) and physiological (pH=7.4) pH values verified the self-elimination mechanism[21]. We sought to utilize this mechanism for the timed (controlled) degradation of the hydrogel. We have used this new mechanism for preparing a self-degradable cross-linked hydrogel that can regulate the release kinetics of a large molecule drug, as well as for degrading the spent hydrogel. The basic skeleton of a cross-linker of the present invention is shown in FIG. 4.

Biodegradable hydrogel with timed degradation of the matrix and/or release of active agents could be used for the subcutaneous delivery of active agents. Hydrogels (polymer/copolymer, crosslinker, and/or active agents) could be subcutaneously administered into the body as solution, where it is converted into the hydrogel in situ due to the intermolecular crosslinking of polymer/copolymer chains. Hydrogel stays into the subcutaneous space and provide controlled-release of active agents (e.g., doxorubicin) into the body. While the hydrogels keep releasing active agents into the body, they simultaneously degrade due to the elimination mechanism describe above, and get converted into soluble PEG molecules, which are naturally cleared from the body without resorting, to surgical or invasive procedures.

These biodegradable hydrogels could also be used for intraductal delivery of active agents into the breast duct for the treatment and image-guided interventions in ductal carcinoma in situ. (DCIS). Ductal carcinoma in situ (DCIS) is a non-invasive, early stage disease that is locally confined to the ductal structure, and considered a step in the progression to invasive breast cancer. Local treatments for breast cancer currently include breast conserving surgery or mastectomy, and may be coupled with radiation therapy. In addition to local therapy, adjuvant systemic therapy may be used including several months of polychemotherapy or years of endocrine therapy for treatment of hormone receptor positive disease. Systemic therapy is also recommended in women for either prevention or treatment of a non-invasive disease. Unfortunately, systemic therapy is often associated with significant side effects. Even non-polychemotherapy such as tamoxifen is associated with frequent bothersome side effects and a few rare, but potentially life-threatening risks. Since the majority of breast cancers originate in the epithelial cells lining the breast duct, administration of agents intraductally (directly into the breast ductal system) provides the opportunity for delivery to the epithelial lining at concentrations not achievable with systemic delivery[22]. The feasibility of intraductal administration has been evaluated in clinical trials, where it was observed that intraductally-administered drug rapidly diffuse into systemic circulation, causing significant side effects.

Biodegradable hydrogel technology could be used to delivery drugs intraductally. Hydrogel (containing drug modified with polymeric carriers and/or targeting moiety) is administered as solution into the breast duct (intraductally), where it forms hydrogel in situ (FIG. 17). The hydrogel depot provides a controlled drug release. However, the drug will not diffuse into the systemic circulation due to its large molecular size and will be taken up by the cancerous cells lining, the ductal epithelium. Thus high local drug concentration is achieved in breast duct accompanied with low systemic toxicities. Finally hydrogel degrades and is cleared from the breast duct and degradation could be timed to match the treatment regimen. (e.g., 30 days). Another approach is to completely remove the diseased ducts by surgery, which is difficult to achieve. Biodegradable hydrogels could be used to deliver imaging agents (dye covalently attached to the hydrogel matrix) to breast ducts (FIG. 17), where it helps identify right margins for the complete removal of ducts during the surgery (image-guided interventions). The degradation is timed so that hydrogels remain stable during the period patients are monitored (~30-60 days) but degrade after this period.

It is an object of the invention to provide a pharmaceutical formulation capable of forming a biodegradable hydrogel in situ to provide timed release of an active agent comprising:

a hydrophilic agent that is a polyethylene glycol polymer or copolymer, a multifunctional polyethylene glycol cross-linker which forms a hydrogel in situ by interaction between functional groups on the cross-linker and functional groups on the hydrophilic agent, a therapeutically effective amount of one or more active agents, and a linker containing an amide bond;

the formulation comprising either;

a) the active agent bonded to the linker, and the linker bonded to the hydrogel wherein the linker containing, an amide bond provides timed cleavage of the active agent from the hydrogel, or b) the active agent passively entrapped in the hydrogel, the cross-linker bonded to the linker, and the linker bonded to the polyethylene glycol polymer or copolymer wherein the linker containing an amide bond provides timed cleavage of the hydrogel structure.

In certain embodiments, the invention is directed to a pharmaceutical formulation capable of forming a biodegradable hydrogel in situ to provide timed release of an active agent comprising:

a hydrophilic agent that is a polyethylene glycol polymer or copolymer, a multifunctional polyethylene glycol cross-linker which forms a hydrogel in situ by interaction between functional groups on the cross-linker and functional groups on the hydrophilic agent, a therapeutically effective amount of one or more active agents, and a linker containing an amide bond;

the formulation comprising either:

a) the active agent bonded to the linker, and the linker bonded to the hydrogel wherein the linker containing an amide bond provides timed cleavage of the active agent from the hydrogel, or b) the active agent passively entrapped in the hydrogel, the cross-linker bonded to the linker, and the linker bonded to the polyethylene glycol polymer or copolymer wherein the linker containing an amide bond provides timed cleavage of the hydrogel structure, or c) the active agent bonded to the hydrogel by non-degradable bonds, or d) combinations of a), b) and c).

In accordance with any of the above objects, the invention is directed to a formulation wherein the polyethylene glycol cross-linker is a bifunctional cross-linker.

In accordance with any of the above objects, the invention is directed to a formulation wherein the active agent is bonded to the hydrogel, by degradable and non-degradable bonds, and is present in a concentration of about 1 to about 10% (w/v).

In accordance with the above object, it is further object of the invention to provide a formulation wherein the passively entrapped active agent is time released independently horn the timed cleavage of the amide bond.

In accordance with any of the above objects, it is further object of the invention to provide a formulation wherein the passively entrapped active agent is time released dependent from the timed cleavage of the amide bond.

In accordance with any of the above objects, it is further object of the invention to provide a formulation wherein the amide bond providing the timed cleavage comprises an amino functional group attached to a γ-carboxyl group, and the cleavage reaction provides a primary amine compound as the leaving group.

In accordance with any of the above objects, it is further object of the invention to provide a formulation wherein the linker comprises glutamic acid bonded to the hydrogel, a γ-carboxylic group of glutamic acid is attached to an active agent through an amide bond, the α-amino group of glutamic acid is free and provides timed cleavage by reacting with the γ-carboxylic group, resulting in cleavage of the γ-amide bond and formation of a five member cyclic ring, and releasing the active agent.

In accordance with any of the above objects, it is further object of the invention to provide a formulation wherein the active agent is passively entrapped and also coupled to the PEG through degradable bonds selected from the group consisting of: enzyme-sensitive peptide linkers, self-immolative linkers, acid and base-sensitive linkers, pH sensitive linkers, multifunctional organic linking agents, multifunctional inorganic crosslinking agents and peptidic backbones represented by the formula: $CH_3CO-(X-Z-Z)_x-(Y-Z-Z)_y-CONH_2$, where X=Lys, Glu, Asp or diaminobutyric acid; Y=Cys, homocysteine or 1-amino-2-methyl-2-propanethiol; Z=β-Ala, Gly, Ala, or GABA (gamma-amino butyric acid); x and y are interchangeable; x is between 1 to 4; y is between 1 to 4; the minimum number of Z-spacer on the peptide backbone is 2; maximum number of Z-spacer on the peptide backbone is 4.

In accordance with any of the above objects, it is further object of the invention to provide a formulation, wherein the hydrophilic agent is a multi-arm thiol-containing PEG, and the crosslinker is a multifunctional PEG cross-linker containing thiol-reactive function groups.

In accordance with any of the above objects, it is further object of the invention to provide a formulation wherein the thiol-reactive function groups are selected from the group consisting of a vinylsulfone, a maleimide and combinations thereof.

In accordance with any of the above objects, it is further object of the invention to provide a formulation wherein the cross-linker contains thiol groups, and the hydrophilic agent is a multi-arm PEG containing thiol-reactive functional groups.

In accordance with any of the above objects, it is further object of the invention to provide a formulation, wherein the thiol-reactive functional groups are selected from the group consisting of a vinylsulfone, a maleimide and combinations thereof.

In accordance with any of the above objects, it is further object of the invention to provide a formulation, wherein the concentration of the hydrophilic polymer or copolymer is from about 1 to about 20% (w/v).

In accordance with any of the above objects, it is further object of the invention to provide a formulation wherein the concentration of the cross-linker is from about 1 to about 15% (w/v).

In accordance with any of the above objects, it is further object of the invention to provide a formulation wherein the ratio of the polymer or copolymer to the cross-linker is from about 0.05:10 to about 10:0.05.

In accordance with any of the above objects, it is further object of the invention to provide a formulation wherein the ratio of the polymer or copolymer to the cross-linker is about 2:0.05.

In accordance with any of the above objects, it is further object of the invention to provide a formulation wherein the polyethylene glycol is a linear or multi-arm having from 2 to 8 arms.

In accordance with any of the above objects, it is further object of the invention to provide a formulation wherein the polyethylene glycol contains multiple thiol groups and has a molecular weight from about 1000-100,000 Da.

In accordance with any of the above objects, it is further object of the invention to provide a formulation wherein the cross-linker is selected horn the group consisting of EMXL ($CONH_2$-Cys(VS)-Glu($NH_2$)-PEG-Glu($NH_2$)-Cys(VS)—$CONH_2$), GABA-EMXL($CONH_2$-Cys(VS)-Glu(GABA-$NH_2$)-PEG-Glu(GABA—$NH_2$)-Cys(VS—)—$CONH_2$), and combinations thereof.

In accordance with any of the above objects, it is further object of the invention to provide a formulation wherein the cross-linker is selected from the group consisting of BM[PEO]$_3$ (1,8-bis-maleimidotriethyleneglycol), BM[PEO]$_4$ (1,11-bis-maleimidotriethyleneglycol), BMH (bis-maleimidohexane), BMOE (bis-baleimidoethane) and combinations thereof.

In accordance with any of the above objects, it is further object of the invention to provide a formulation wherein the cross-linker is selected from the group consisting of rEMXL, dithiothreitol, polycysteines, PEG-dithiol, a 4-arm thiol and combinations thereof.

In accordance with any of the above objects, it is further object of the invention to provide a formulation wherein the active agent is present in a concentration of about 0.1 to about 12% (w/v, and is passively entrapped in the hydrogel.

In accordance with any of the above objects, it is further object of the invention to provide a formulation wherein the active agent is bonded to the hydrogel, and is present in a concentration of about 1 to about 10% (w/v).

In accordance with any of the above objects, it is further object of the invention to provide a formulation wherein the active agent is selected from the group consisting of: anti-inflammatory drugs, NSAID analogs. NSAID-ache (NSAID-acetylcholinesterase complexes, steroidal anti-inflammatory drugs, anticancer drugs, HIV protease inhibitors, monoclonal antibodies, imaging agents, and combinations thereof.

In accordance with any of the above objects, it is further object of the invention to provide a formulation wherein the active agent is selected from the group consisting of: indomethacin, sancycline, a sancycline analog, olvanil, an olvanil analog, retro-olvanil, a retro-olvanil analog, olvanil carbamate, budesonide, a budesonide analog, methylprednisolone, a methylprenisolone analog, dexamethasone, a dexamethasone analog, camptothecin, carboplatin, doxorubicin, paclitaxel, saquinavir mesylate, amprenavir, ritonavir, indinavir, netfinavir mesylate, tipranavir, darunavir, atazanavir sulfate, a coloring dye, an FD and C dye, a visible/near infrared fluorescence dye, fluorescein, methylene blue, rhodamine, dansyl, Alexa, a cyanine dye, Hilyte, indocyanine green, and combinations thereof.

In accordance with any of the above objects, it is further object of the invention to provide a formulation wherein the active agent is modified with a targeting moiety selected from the group consisting of: an RGD peptide, EGF peptide, DV3 (LGASWHRPDKC) peptide, a LYP peptide (CGNKRTRGC), membrane-binding domain of IGFBP3 (QCRPSKGRKRGFCW), fMLF, mannose, transferrin ligand, and monoclonal antibodies.

In accordance with any of the above objects, it is further object of the invention to provide a formulation wherein the active agent is doxorubicin which is modified with a targeting moiety selected from the group consisting of: Leu-Gly, Glu(Leu-Gly)$_2$, Arg-Gly-Asp-Cys, Gly-Arg-Gly-Asp-Ser, Gly-Arg-Gly-Asp-Ser-Pro, cyclic Arg-Gly-Asp-Tyr-Lys, any peptide with Arg-Gly-Asp, and combinations thereof.

It is further object of the invention to provide a method of preparation of the formulation in accordance with any of the above objects wherein the cross-linker comprises vinylsulfone groups, the method comprising:

reacting, a diamino-PEG having from 2 to 8 arms and a molecular weight from about 1 to about 20 kDa with Dde-Glu-(γCOOH)-Cys(StBu)—$CONH_2$ or Dde-AA-Glu-(γCOOH)-Cys(StBu)—$CONH_2$ from both sides in DMF to obtain (Dde-AA-$R_1$-SStBu)$_2$PEG, wherein AA is selected from the group consisting of GABA (γ-amino butyric acid); AHA (6-aminohexanoic acid), AOA (8-aminooctanoic acid), GABA-GABA, AHA-AHA, AOA-AOA, AHA-GABA, AOA-GABA, AHA-GABA and combinations thereof, removing the -StBu protecting groups presets in $R_1$ by treatment with DTT to produce two unprotected —SH groups, reacting the two unprotected —SH groups with HBVS to introduce VS moieties on the two termini, and removing the Dde-groups by treating with hydrazine.

It is further object of the invention to provide a method of preparation of the formulation in accordance with any of the above objects wherein the cross-linker comprises maleimide groups, the method comprising:

reacting diamino-PEG having from 2 to 8 arms and a molecular weight from about 1 to about 20 kDa with Dde-Glu-(γCOOH)-Cys(StBu)—$CONH_2$ or Dde-AA-Glu-(γCOOH)-Cys(StBu)—$CONH_2$ from both sides in DME to obtain (Dde-AA-$R_1$-SStBu)$_2$PEG, wherein AA is selected from the group consisting of GABA, AHA, AOA, GABA-GABA, AHA-AHA, AOA-AOA, AHA-GABA, AOA-GABA, AHA-GABA, and combinations thereof, removing the -StBu protecting group presets in $R_1$ by treatment with DTT to produce two unprotected thiol groups;

reacting the two unprotected thiol groups with a cross-linker selected from the group consisting of BM[PEO]$_3$ (1,8-bis-maleimidotriethyleneglycol), BM[PEO]$_4$ (1,1-bis-maleimidotriethyleneglycol), BMH (bis-maleimidohexane), BMOE (bis-maleimidoethane) and combinations thereof to incorporate maleimide groups on the two termini, and removing the Dde-group by treating with hydrazine.

It is further object of the invention to provide a method of preparation of the formulation in accordance with any of the above objects by reverse chemistry, wherein the cross-linker comprises thiol groups, the method comprising:

reacting a diamino-PEG having from 2 to 8 arms and a molecular weight of about 1 to about 20 kDa with Dde-Glu-(γCOOH)-Cys(StBu)—$CONH_2$ or Dde-AA-Glu-(γCOOH)-Cys(StBu)—$CONH_2$ wherein AA is selected from the group consisting of GABA, AHA, AOA, GABA-GABA, AHA-AHA, AOA-AOA, AHA-GABA, AOA-GABA, AHA-GABA, from both sides in DMF to obtain (Dde-AA-$R_1$-SStBu)$_2$PEG, removing the -StBu protecting group presets in $R_1$ by treatment with DTT, and removing the Dde-groups by treatment with hydrazine.

It is further object of the invention to provide a method of preparation of the polymer containing terminal thiol for use in the formulation in accordance with any of the above objects comprising:

reacting diamino-PEG having from 2 to 8 arms and a molecular weight of from about 1 to about 20 kDa, with Dde-Glu-(γCOOH)-Cys(StBu)—CONH$_2$ or Dde-AA-Glu-(γCOOH)-Cys(StBu)—CONH$_2$ wherein AA is GABA, AHA, AOA, GABA-GABA, AHA-AHA, AOA-AOA, AHA-GABA, AOA-GABA, AHA-GABA, from both sides in DMF to obtain (Dde-AA-R$_1$-SStBu)$_2$PEG, removing the -StBu protecting group presets in R$_1$ by treatment with DTT, and removing the Dde-groups by treatment with hydrazine.

It is further object of the invention to provide a method of preparation of the formulation in accordance with any of the above objects wherein the cross-linker comprises vinylsulfone groups, the method comprising:

reacting a diamino-PEG having more then 2 arms and a molecular weight from about 1 to about 20 kDa with Dde-Glu-(γCOOH)-Cys(StBu)—CONH$_2$ or Dde-AA-Glu-(γCOOH)-Cys(StBu)—CONH$_2$ from both sides in DMF to obtain (Dde-AA-R$_1$-SStBu)$_2$PEG, wherein AA is selected from the group consisting of GABA(γ-amino butyric acid); AHA (6-aminohexanoic acid). AOA (8-aminooctanoic acid), GABA-GABA, AHA-AHA, AOA-AOA, AHA-GABA, AOA-GABA, AHA-GABA and combinations thereof, removing the -StBu protecting groups presets in R$_1$ by treatment with DTT to produce two unprotected —SH groups, reacting the two unprotected—SH groups with HBVS to introduce VS moieties on the two termini, and removing the Dde-groups by treating with hydrazine.

It is further object of the invention to provide a method of preparation of the formulation in accordance with any of the above objects wherein the cross-linker comprises maleimide groups, the method comprising:

reacting diamino-PEG having more then 2 arms and a molecular weight from about 1 to about 20 kDa with Dde-Glu-(γCOOH)-Cys(StBu)—CONH$_2$ or Dde-AA-Glu-(γCOOH)-Cys(StBu)—CONH$_2$ from both sides in DMF to obtain (Dde-AA-R$_1$-SStBu)$_2$PEG, wherein AA is selected from the group consisting of GABA, AHA, AOA, GABA-GABA, AHA-AHA, AOA-AOA, AHA-GABA, AOA-GABA, AHA-GABA, and combinations thereof, removing the -StBu protecting group presets in R$_1$ by treatment with DTT to produce two unprotected thiol groups;

reacting the two unprotected thiol groups with a cross-linker selected from the group consisting of BM[PEO]$_3$ (1,8-bis-maleimidotriethyleneglycol), BM[PEO]$_4$ (1,11-bis-maleimidotriethyleneglycol), BMH (bis-maleimidohexane), BMOE (bis-maleimidoethane) and combinations thereof to incorporate maleimide groups on the two termini, and removing the Dde-group by treating with hydrazine.

It is further object of the invention to provide a method of preparation by reverse chemistry, of the formulation in accordance with any of the above objects wherein the cross-linker comprises thiol groups, the method comprising:

reacting a diamino-PEG having more then 2 arms and a molecular weight of about 1 to about 20 kDa with Dde-Glu-(γCOOH)-Cys(StBu)—CONH$_2$ or Dde-AA-Glu-(γCOOH)-Cys(StBu)—CONH$_2$ wherein AA is selected from the group consisting of GABA, AHA, AOA, GABA-GABA, AHA-AHA, OA-AOA, AHA-GABA, AOA-GABA, AHA-GABA, from both sides in DMF to obtain (Dde-AA R$_1$-SStBu)$_2$PEG, removing the -StBu protecting group presets in R$_1$ by treatment with DTT, and removing the Dde-groups by treatment with hydrazine.

It is further object of the invention to provide a method of treatment comprising administering a formulation in accordance with an of the above objects. In certain embodiments, the active agent is administered subcutaneously. In certain embodiments, the active agent is administered intraductally. In certain embodiments, the timed release of the active agent is from about 1 min to about 1440 h. In certain embodiments, the timed release of the active agent is from about 1 min to about 720 h. In certain embodiments, the timed release of the active agent is from about 1 min to about 490 h. In certain embodiments, the timed release of the active agent is from about 1 min to about 360 h. In certain embodiments, the timed release of the active agent is from about 1 min to about 336 h. In certain embodiments, the timed release of the active agent is from about 1 min to about 119 h. In certain embodiments, the timed release of the active agent is from about 1 min to about 72 h. In certain embodiments, the timed release of the active agent is from about 1 min to about 47 h. In certain embodiments, the timed release of the active agent is from about 1 min to about 29.5 h. In certain embodiments, the timed release of the active agent is from about 1 min to about 17.5h. In certain embodiments, the timed release of the active agent is from about 1 min to about 10 h. In certain embodiments, the timed degradation of the hydrogel is from about 1 h to about 2160 h. In certain embodiments, the timed degradation of the hydrogel is from about 1 h to about 720 h. In certain embodiments; the timed degradation of the hydrogel is from about 1 h to about 490 h. In certain embodiments, the timed degradation of the hydrogel is from about 1 h to about 360 h. In certain embodiments, the timed degradation of the hydrogel is from about 1 h to about 336 h. In certain embodiments, the timed degradation of the hydrogel is from about 1 h to about 119 h. In certain embodiments, the timed degradation of the hydrogel is from about 1 h to about 72 h. In certain embodiments, the timed degradation of the hydrogel is from about 1 h to about 47 h. In certain embodiments, the timed degradation of the hydrogel is from about 1 h to about 29.5 h. In certain embodiments, the timed degradation of the hydrogel is from about 1 H to about 17.5 h. In certain embodiments, the timed degradation of the hydrogel is from about 1 H to about 10 h.

DETAILED DESCRIPTION OF THE INVENTION

Degradable Hydrogels

Figure 1:
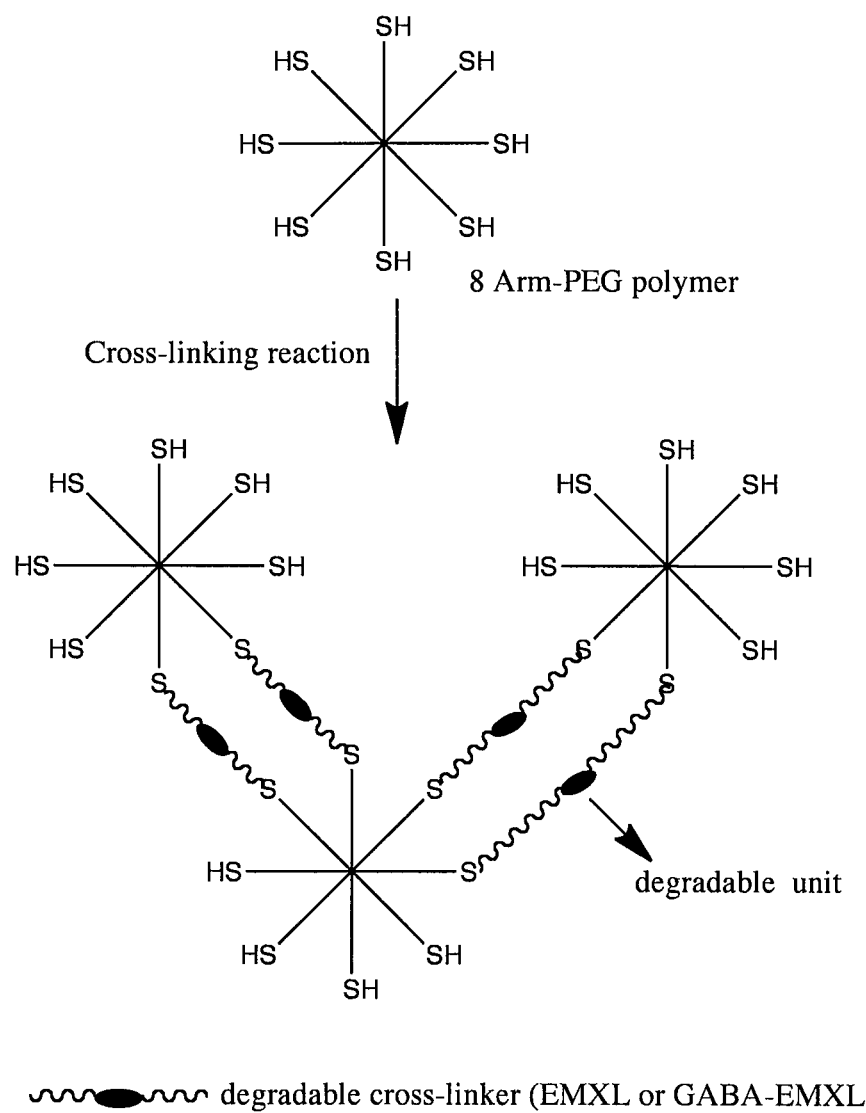
FIG. 1. Schematic presentation of biodegradable hydrogel formation.
Figure 2:
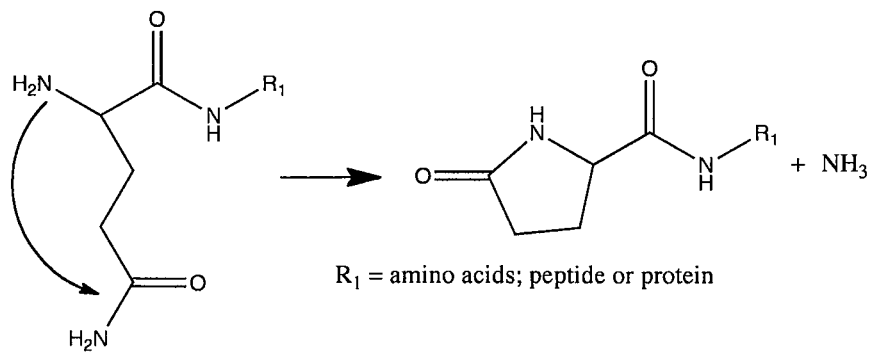
FIG. 2. Glutamine residue is converted to the cyclic analog, pyroglutamic acid, and ammonia is released.
Figure 3:
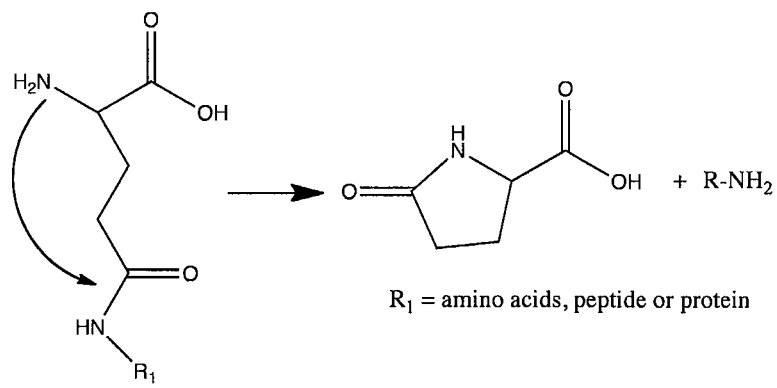
FIG. 3. New mechanism: glutamine residue is converted to the cyclic analog, pyroglutamic acid, and a free primary amine is released.
Figure 4:
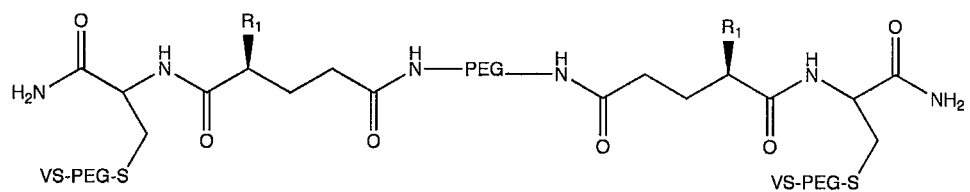
FIG. 4. Basic skeleton of biodegradable PEG crosslinkers.
Figure 5:
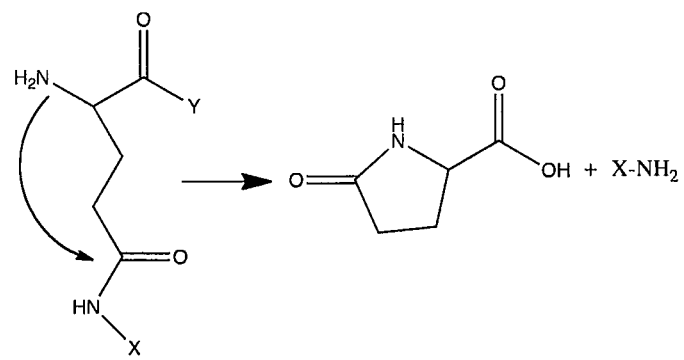
FIG. 5. Schematic representation of the invention, wherein X represents the active agents or hydrogel matrix.
Figure 6:
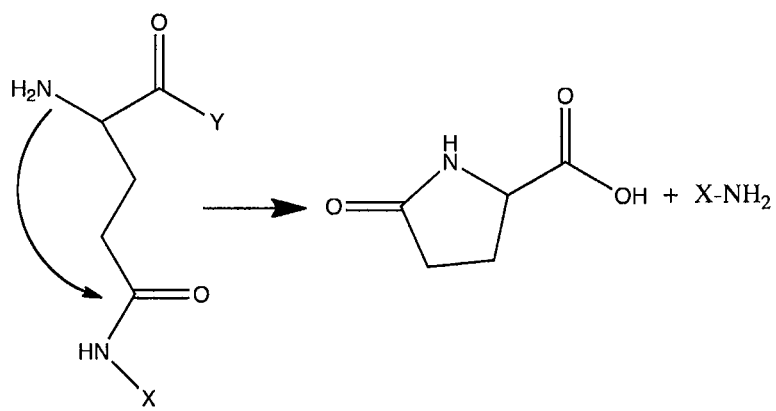
FIG. 6. Schematic representation of the invention, wherein X represents the hydrogel matrix.

Elimination reaction causing timed (controlled) degradation of hydrogel. Incorporation of a compound having a nucleophilic moiety such as Glutamic acid (GM) or γ-aminobutyric acid in the linker gives rise to the elimination mechanism. The γ-carboxylic group of Glu is attached to a cross-linker unit via an amide bond. The α-amino group of the Glu is free. In this reaction, the free amino group of Glu attacks its own γ-carboxylic group, resulting, in cleavage of the γ amide bond to form a five member cyclic ring. Breakage of the amide bond gives the driving force for the degradation of the hydrogel matrix. FIGS. 5 and 6 shows the elimination reaction (basic mechanism causing the timed degradation of hydrogel matrix.

Figure 7:
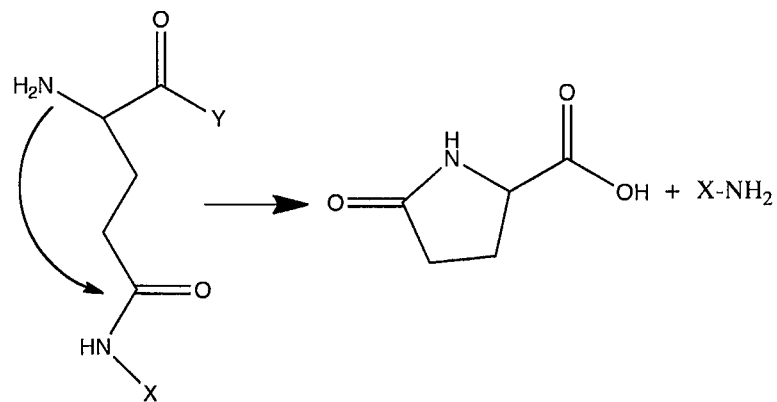
FIG. 7. Schematic representation of the invention, wherein X represents the active agents.
Figure 8:
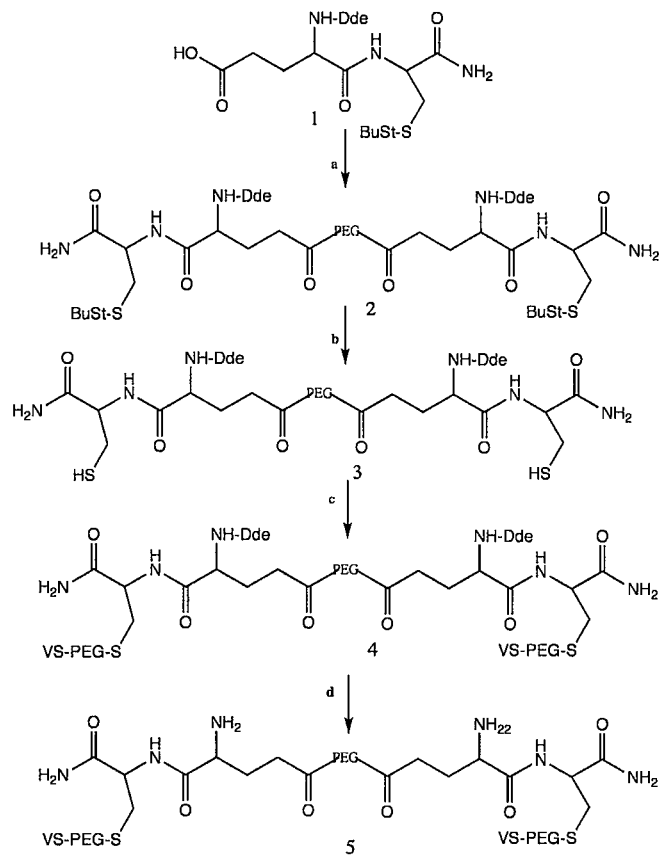
FIG. 8. Synthesis of biodegradable crosslinker: EMXL (compound 5).

Elimination reaction causing timed (controlled) release of active agents from hydrogel. Glutamic acid (Glu) is the central component in the elimination mechanism. The γ-carboxylic group of Glu is attached to an active agent through an amide bond. The α-amino group of Glu is free, which attacks its own γ-carboxylic group, resulting in cleavage of the γ-amide bond and formation of a five member cyclic ring. Breakage of the amide bond gives the driving force for the release of active agent. FIG. 7 shows the elimination reaction (basic mechanism) causing the release of active agents front the hydrogel.

General procedure for hydrogel formation. Hydrogels are formed in situ by reaction between a multivalent copolymer or PEG polymer and cross-linker in aqueous medium. Several combinations are possible: (i) the PEG polymer or copolymer contain thiol groups whereas the crosslinker has thiol-reactive vinylsulfone; maleimide etc. groups; or (ii) the crosslinker contain thiol groups whereas PEG polymer or copolymer contains thiol-reactive vinylsulfone, maleimide etc. groups ("reverse chemistry"). The hydrogels disclosed herein can be obtained over a broad concentration range of the polymers or copolymers, and crosslinkers. The concentration ranges of the polymer or copolymer is 1%-20(w/v) and that of the crosslinker is 1%-15% (w/v). The ratios of the polymer or copolymer to the crosslinker in the hydrogel vary from 0.05:10 to 10:0.05 and preferably 2:0.05. Either single type of polymer/copolymer and crosslinker is used or a combination of different types of unmodified and modified copolymer or polymer and crosslinkers is used.

Polymers for hydrogel formation. Linear or multi-arm PEG having 2 or more arms, and preferably PEG having 2 to 8 arms containing multiple thiol groups (more than 1) with in a molecular weight range: 1000-100,000 Da. Polymers could be unmodified or modified with active agents (timed-release mechanism, other degradation mechanism, or non-degradable) prior to hydrogel formation.

Copolymer containing thiol groups. The invention can be extended to copolymers containing repeating units of thiol groups. For example, copolymer like poly[poly(ethylene glycol)-alt-poly (mercaptosuccinic acid)][23] in the molecular weight range of 10,000 to 100,000 Da. Copolymers could be unmodified or modified with active agents (timed-release mechanism, other degradation mechanism, or non-degradable) prior to hydrogel formation.

Polymer containing peptide thiol groups. The invention can be extended to polymers containing repeating units of peptide thiol groups such as polycysteine in the molecular weight range of 1,000 to 100,000 Da. Polymers could be unmodified or modified with active agents (timed-release mechanism, other degradation mechanism, or non-degradable) prior to hydrogel formation. The polymer containing terminal thiol groups based on elimination mechanism were obtained by reacting diamino-PEG (preferably 2-8 arms, MW ~1-20 kDa) with Dde-Glu-(γCOOH)-Cys(StBu)—$CONH_2$ or Dde-AA-Glu-(γCOOH)-Cys(StBu)—$CONH_2$ [AA is GABA, AHA, AOA, GABA-GABA, AHA-AHA, AOA-AOA, AHA-GABA, AOA-GABA, AHA-GABA] from both sides in DMF to obtain (Dde-AA-$R_1$-SStBu)$_2$PEG. The -StBu protecting group presets in $R_1$ were removed by treatment with DTT and the Dde-groups were removed by hydrazine.

Cross-linkers for hydrogel formation. Crosslinkers containing functional groups like vinyl sulfone and maleimide groups or thiol groups (for reverse chemistry) are used for hydrogel formation through thioether bonds. Crosslinkers could be linear or branched, contain preferably 2-8 functional groups in the molecular weight range of 1-20 kDa.

Cross-linkers containing vinylsulfone groups. The cross-linkers containing terminal vinylsulfone (VS) functional groups like EMXL ($CONH_2$-Cys(VS)-Glu($NH_2$)-PEG-Glu($NH_2$)-Cys(VS)—$CONH_2$), GABA-EMXL($CONH_2$-Cys(VS)-Glu(GABA-$NH_2$)-PEG-Glu(GABA-$NH_2$)-Cys(VS-)—$CONH_2$) and 1,6-Hexane-bis-vinylsulfone (HBVS) were used.

The crosslinkers based on elimination mechanism were prepared by reacting diamino-PEG (preferably 2-8 arms, MW ~1-20 kDa) with Dde-Glu-(γCOOH)-Cys(StBu)—$CONH_2$ or Dde-AA-Glu-(γCOOH)-Cys(StBu)—$CONH_2$ [AA is GABA(γ-amino butyric acid); AHA (6-aminohexanoic acid); AOA (8-aminooctanoic acid); GABA-GABA; AHA-AHA; AOA-AOA; AHA-GABA; AOA-GABA; AHA-GABA etc.] from both sides in DMF to obtain (Dde-AA-$R_1$-SStBtu)$_2$PEG. The -StBu protecting groups presets in $R_1$ were removed with DTT and the two unprotected—SH groups were reacted with HBVS to introduce VS moieties on the two termini. Finally the Dde-groups were removed by hydrazine (FIGS. 8-9 and 10-11).

Cross-linkers containing maleimide groups (MA). Crosslinkers containing terminal maleimide groups like BM[PEO]$_3$ (1,8-bis-maleimidotriethyleneglycol) or BM[PEO]$_4$ (1,11-bis-maleimidotriethyleneglycol) or BMH (bis-maleimidohexane) or BMOE (bis-baleimidoethane) can also be used.

The maleimide (MA)-containing crosslinker based on elimination mechanism were obtained by reacting diamino-PEG (preferably 2-8 arms, MW ~1-20 kDa) with Dde-Glu-(γCOOH)-Cys(StBu)—CONH$_2$ or Dde-AA-Glu-(γCOOH)-Cys(StBu)—CONH$_2$, [AA is GABA, AHA, AOA, GABA-GABA, AHA-AHA, AOA-AOA, AOA-GABA, AHA-GABA from both sides in DMF to obtain (Dde-AA-R$_1$-SStBu)$_2$PEG. The -StBu protecting group presets in R$_1$ were removed with DTT and the two unprotected thiol groups were reacted with BM[PEO]$_3$ (1,8-bis-maleimidotriethyleneglycol) or BM[PEO]$_4$ (1,11-bis-maleimidotriethyleneglycol) or BMH (bis-maleimidohexane) or BMOE (bis-maleimidoethane) to incorporate maleimide groups on the two termini. Finally, the Dde-group was removed by hydrazine.

Figure 12:
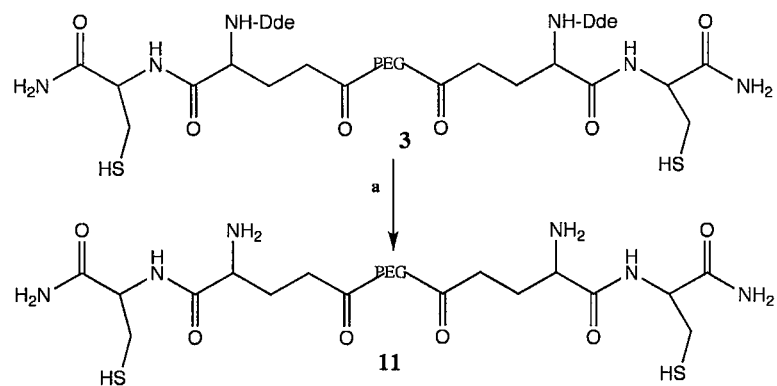
FIG. 12. Synthesis of rEMXL (compound 11).
Figure 13:
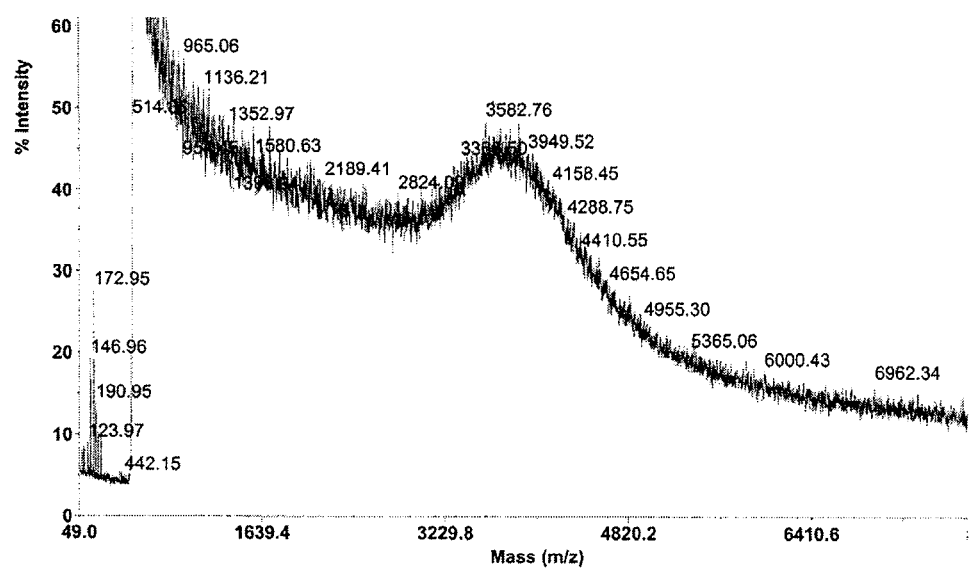
FIG. 13. MALDI-TOF mass spectrum of diamino-PEG after hydrogel degradation.

Cross-linkers containing thiol groups (reverse chemistry). For reverse chemistry, thiol-containing crosslinkers such as dithiothreitol, polycysteines. PEG-dithiol or 4-arm thiol can be used. The crosslinkers containing terminal thiol groups (rEMXL) based on elimination mechanism were obtained by reacting diamino-PEG (preferably 2-8 arms, MW ~1-20 kDa) with Dde-Glu-(γCOOH)-Cys(StBu)—CONH$_2$ or Dde-AA-Glu-(γCOOH)-Cys(StBu)—CONH$_2$ [AA is GABA, AHA, AOA, GABA-GABA, AHA-AHA, AOA-AOA, AHA-GABA, AOA-GABA, AHA-GABA] from both sides in DMF to obtain (Dde-AA-R$_1$-SStBu)$_2$PEG. The -StBu protecting group presets in R$_1$ were removed by treatment with DTT and the Dde-groups were removed by hydrazine (FIG. 12).

Active agents. The active agent preferably comprises an agent selected from the group consisting of anti-inflammatory drugs, NSAID analogs, NSAID-ache (NSAID-acetylcholinesterase complexes, steroidal anti-inflammatory drugs, anticancer drugs, HIV protease inhibitors, monoclonal antibodies, imaging agents, and combinations thereof. In certain other embodiments, the agent is selected from the group consisting of one or more of the following: indomethacin, sancycline, a sancycline analog, olvanil, an olvanil analog, retro-olvanil, a retro-olvanil analog, olvanil carbamate, budesonide, a budesonide analog, methylprednisolone, a methylprenisolone analog, dexamethasone, a dexamethasone analog, camptothecin, carboplatin, doxorubicin, paclitaxel, saquinavir mesylate, amprenavir, ritonavir, indinavir, nelfinavir mesylate, tipranavir, darunavir, DMI a maytansinoid, atazanavir sulfate, a coloring dye, an FD and C dye, a visible/near infrared fluorescence dye, fluorescein, methylene blue, rhodamine, dansyl, Alexa, a cyanine dye. Hilyte, indocyanine green, and combinations thereof. More preferably, the agent is doxorubicin.

For passive entrapment, the agent may be unmodified or coupled to the PEG through degradable bonds (prodrugs) like enzyme-sensitive peptide linkers, self-immolative linkers, acid and base-sensitive linkers, pH sensitive linkers, multifunctional organic linking agents, multifunctional inorganic crosslinking agents and/or peptidic backbones represented as: CH$_3$CO—(X—Z—Z)$_x$—(Y—Z—Z)$_y$—CONH$_2$, where X=Lys, Glu, Asp or diaminobutyric acid; Y=Cys, homocysteine or 1-amino-2-methyl-2-propanethiol; Z=β-Ala, Gly, Ala, or GABA (gamma-amino butyric acid); x and y are interchangeable; x is between 1 to 4; y is between 1 to 4; minimum number of Z-spacer on the peptide backbone=2; maximum number of Z-spacer on the peptide backbone=4.

In variations, the active agent may further comprise a targeting moiety. The targeting moiety may be a peptide, and preferably such a peptide is an RGD peptide. In certain other embodiments, the targeting group is selected from the group consisting of an RGD peptide, EGF peptide, DV3 (LGASWHRPDKC) peptide, a LYP peptide (CGNKRTRGC), membrane-binding domain of IGFBP3 (QCRPSKGRKRGFCW), fMLF, mannose, transferrin ligand, and monoclonal antibodies. When the drug is doxorubicin, the linker used is any of following: Len-Gly, Glu (Leu-Gly)$_2$, Arg-Gly-Asp-Cys, Gly-Arg-Gly-Asp-Ser, Gly-Arg-Gly-Asp-Ser-Pro, cyclic Arg-Gly-Asp-Tyr-Lys or any peptide with Arg-Gly-Asp.

For timed-release of active agents, active agents containing amino groups or active agents modified with amino linker are attached to the γ-carboxyl of Glu. The active agents could be unmodified or attached to carriers as described above. In variations, the active agent may contain targeting unit selected from the targeting groups listed above.

Either for passive entrapment or timed release, single active agent could be used or combinations thereof and the active agent content in the hydrogel formulation may vary from 0.1-12% (w/v).

The general procedure for release of active agents from hydrogels preferably involves the following two processes:

Passive entrapment and release. In one embodiment, the active agent(s) are physically entrapped into the hydrogel by mixing it in the formulation (polymer/copolymer and crosslinker) prior to hydrogel formation. The active agent content in the hydrogel formulation may vary from 0.1-12% (w/v) and the formulation may contain one active agent or a combination thereof. The release of the active agent from the hydrogel is not directly dependent on the hydrogel degradation mechanism. Alternatively, the active agent can be free from the hydrogel before the hydrogel matrix degrades. Therefore, the release of the active agent from the hydrogel is not dependent on the elimination mechanism.

Timed release of active agents. Active agents containing amino groups or modified with a linker containing amino groups are linked to the γ-carboxyl of Glu. They are released following the elimination reaction as shown in FIG. 7. The active agents or modified active agents with a linker could be attached to the polymer/crosslinker and the active agent content may vary from 1-10% (w/v). Alternatively, the active agent can be free in the hydrogel matrix from the modified linker. Therefore, the release of the active agent from the hydrogel is indirectly dependent on the elimination mechanism.

The invention is described more fully by way of the following non-limiting examples. All references cited above and hereafter in this document are hereby incorporated by reference in their entirety herein.

DETAILED DESCRIPTION OF THE PREFERRED EMBODIMENTS

The cross-linker is the control component in this biodegradable hydrogel. The hydrogel was obtained by irreversibly cross-linking a thiol terminated PEG polymer or copolymer such as 8-arm PEG—SH and crosslinkers [(EMXL), GABAEMXL, 1,6-Hexane-bis-vinylsulfone (HBVS)] in phosphate buffer (pH, 7.4) at room temperature. Unless otherwise indicated, the hydrogel formation, release, and degradations studies have been done in triplicate.

EXAMPLE 1

Synthesis of Biodegradable EMXL Crosslinker

Dde-Glu-(γCOOH)-Cys(StBu)—CONH$_2$ [Dde-R$_1$-SStBu] was coupled to diamino-PEG (DAP, 3350 Da) from both sides in DMF to obtain (Dde-R$_1$-SStBu)$_2$PEG. The -StBu protecting group presets in R$_1$ were removed by treatment with DTT and the two unprotected thiol (—SH) groups were reacted with HBVS to introduce VS moieties on the two termini (FIG. 8), Synthesis of EMXL (see FIG. 8)

Step 1

Preparation of Compound 2

The DAP polymer (1 eq, Catalog #P9906-5G, Sigma Aldrich, St. Louis, Mo.) was weighed in a 100 mL round bottom flask and DMF (10.0 mL, Catalog #354830025, Across Organics, Morris Plains, N.J.) was added. DIEA (7 eq, Catalog #387649-100, Sigma Aldrich, St. Louis, Mo.) was added into the flask and the mixture was gently stirred (1000 rpm) at room temperature (24° C.) for 5 min to activate the both amino groups of DAP at room temperature. Dde-R$_1$-SStBu (7 eq) and PyBOP (7 eq, Catalog #01-62-0016, Novabiochem, San Diego, Calif.) in DMF (10 ml) were added into reaction mixture. The reaction mixture was stirred at (1000-1500 rpm) for 6-20 h at room temperature (24° C.) for ~8 hours. After 8 hours, the stirring, was stopped.

Purification of Compound 2

The reaction mixture was purified by Sephadex LH-20 using DMF as the eluent. Sephadex LH-20 medium gel filtration media (Catalog #17-0090-01, VWR international, Pittsburgh, Pa.) was soaked in DMF (25 mg/500 mL, Catalog #354830025. Across Organics, Morris Plains, N.J.) at room temperature (25° C.) for 24 hours. The presoaked Sephadex was loaded on to the column. The reaction mixture (10×1.0 mL) was loaded onto the column and eluted using DMF; the collected DMF fractions was poured dropwise into precooled diethyl ether (60 ml) to precipitate the product. The product was dried under argon gas. Yield. 88%.

Step 2

Preparation of Compound 3

The compound 2 (1 eq,) and DTT (11.5 eq, Catalog #D5545, Sigma Aldrich, St. Louis, Mo.) were weighed in a 100 mL round bottom flask and DMF (10.0 mL, Catalog #354830025, Across Organics, Morris Plains, N.J.) was added. Na$_2$CO$_3$ (1 eq, Catalog. #144-55-8, EM Industries, Hawthorne, N.Y.) was added into the reaction mixture. The reaction mixture was gently stirred (1000 rpm) at room temperature (24° C.) for 24 h. After 24 h, the stirring was stopped and the reaction mixture was poured drop wise into precooled diethyl ether (60 ml) to precipitate the crude product. The crude reaction mixture was used "as is" for the next step without purification. Yield. 70%.

Step 3

Preparation of Compound 4

Compound 3 (1 eq) and HBVS (40 eq, 1,6-Hexane-bis-vinylsulfone Catalog #2234, Pierce, Rockford, Ill.) were weighed in a 100 mL round bottom flask and DMF (10.0 mL, Catalog #354830025, Across Organics, Morris Plains, N.J.) was added. DIEA (2 eq, Catalog #387649-100 Sigma Aldrich, St. Louis, Mo.) was added into the flask and the mixture was gently stirred (1000 rpm) at room temperature (24° C.) for ~8 hours. After 8 hours, the stirring was stopped.

Purification of Compound 4

The reaction mixture was purified by Sephadex LH-20 using DMF as eluent. Sephadex LH-20 medium gel filtration media (Catalog #17-0090-01, VWR International, Pittsburgh, Pa.) Was soaked in DMF (25 mg/500 mL, Catalog #354830025, Across Organics, Morris Plains, N.J.) at room temperature (25° C.) for 24 hours. The presoaked Sephadex was loaded on to the glass column. The reaction mixture (10×1.0 mL) was loaded onto the column and eluted using DMF; the collected. DMF fractions were poured dropwise into precooled diethyl ether (60 ml) to precipitate the product. The product was dried under argon gas. Yield. 81%.

Step 4

Preparation of Compound 5

Compound 4 (0.059 g) was weighed in a 100 mL round bottom flask and hydrazine (3% in DMF, Catalog #303400-5G, Sigma Aldrich, St. Louis, Mo.) was added into the flask. The reaction mixture was gently stirred (1000 rpm) at room temperature (24° C.) for ~3 hours. After 3 hours, the stirring was stopped.

Purification of Compound 0.5

Figure 9:
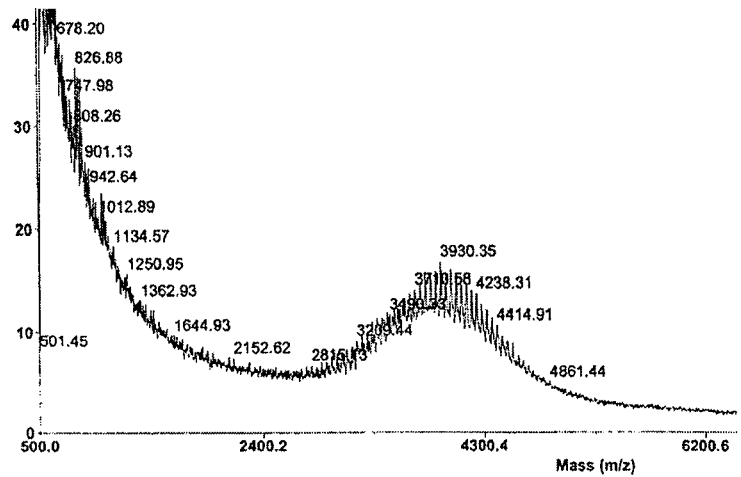
FIG. 9. MALDI-TOF mass spectrum of EMXL (compound 5).

The reaction mixture was purified by Sephadex LH-20 using DMF as eluent. Sephadex LH-20 medium gel filtration media (Catalog #17-0090-01, VWR International, Pittsburgh, Pa.) was soaked in DMF (25 mg/500 ml, Catalog #354830025, Across Organics, Morris Plains, N.J.) at room temperature (25° C.) for 24 hours. The presoaked Sephadex was loaded on to the glass column. Reaction mixture (10×1.0 mL) was loaded onto the column and eluted using DMF. The collected DMF fractions were poured dropwise into precooled diethyl ether (60 ml) to precipitate the product. The product was dried under argon gas. Yield obtained was 70%. The product was characterized by MALDI-TOF mass spectrometry (MS) (FIG. 9).

EXAMPLE 2

Synthesis of Biodegradable GABAEMXL Crosslinker

Figure 10:
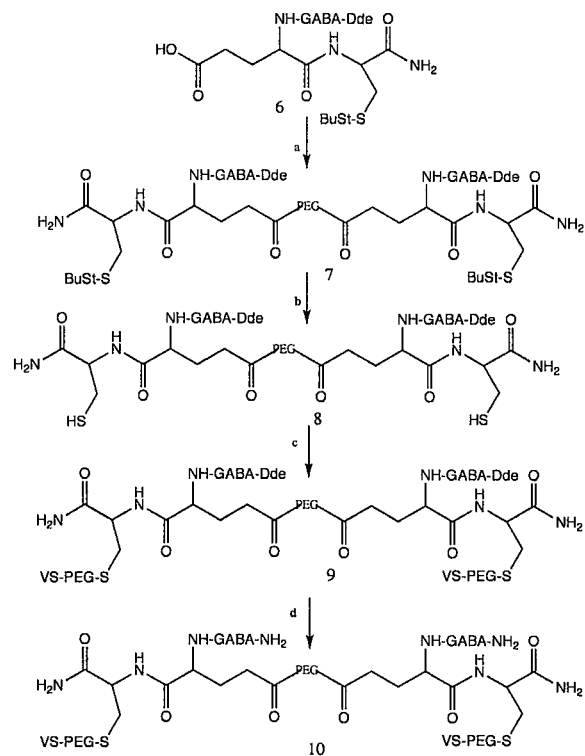
FIG. 10. Synthesis of biodegradable crosslinker: GABAEMXL (compound 10).

The biodegradable crosslinker GABA-EMXL (EMXL with γ-amino butyric acid attached to N-terminal of Glu) was prepared using NH$_2$-PEG—NH$_2$ (3350 Da). Dde-GABA-Glu-(γCOOH)-Cys(StBu)—CONH$_2$[R$_2$] [Dde-GABA-R$_2$-SStBu] was coupled with diamino-PEG from both sides in DMF to obtain (Dde-GABA-R$_2$-SStBu)$_2$PEG. The -StBu protecting group presets in R$_2$ were removed by treatment with DTT and the two unprotected —SH groups were reacted with HBVS to introduce VS moieties on the two termini (FIG. 10).

Step 1

Preparation of Compound 7

The DAP polymer (1 eq, Catalog #P9906-5G. Sigma Aldrich, St. Louis, Mo.) was weighed in a 100 mL round bottom flask and DMF (10.0 mL; Catalog #354830025. Across Organics, Morris Plains, N.J.) was added. DIEA (7 eq; Catalog #387649-100 ml, Sigma Aldrich, St. Louis, Mo.) was added into the flask and the mixture was gently stirred (1000 rpm) at room temperature (24° C.) for 5 min to activate the both amino groups of DAP at room temperature. Dde-GABA-R$_2$-SStBu (7 eq) and PyBOP (7 eq, Catalog #01-62-0016 Novabiochem, San Diego, Calif.) in DMF (10 ml;) were added into reaction mixture. The reaction mixture was stirred at (1000-1500 rpm) for 6-20 h at room temperature (24° C.) for ~8 hours. After 8 hours, the stirring was stopped.

Purification of Compound 7

The reaction mixture was purified by Sephadex LH-20 using DMF as eluent. Sephadex LH-20 medium gel filtration media (Catalog #17-0090-01, VWR International, Pittsburgh, Pa.) was soaked in DMF (25 mg/500 mL, Catalog #354830025, Across Organics, Morris Plains, N.J.) at room temperature (25° C.) for 24 hours. The presoaked Sephadex was loaded on to the glass column. The reaction mixture (10×1.0 mL) was loaded onto the column and eluted using DMF. The collected DMF fractions were poured dropwise into pre-cooled diethyl ether (60 ml) to precipitate the product. The product was dried under argon gas. Yield, 88%.

Step 2

Preparation of Compound 8

The compound 7 (1 eq) and DTT (11.5 eq, Catalog #D5545, Sigma Aldrich, St. Louis, Mo. 63178, USA) were weighed in a 100 mL round bottom flask and DMF (10.0 mL, Catalog #354830025. Across Organics, Morris Plains, N.J.) was added, $Na_2CO_3$ (1 eq, Catalog #144-55-8, EM Industries, Hawthorne, N.Y.) was added into the reaction mixture. The reaction mixture was gently stirred at (1000 rpm) at room temperature (24° C.) for 24 h. After 24 h, the stirring was stopped and the reaction mixture was poured drop wise into pre-cooled diethyl ether (60 ml) to precipitate the crude product. The crude reaction mixture was used "as is" for the next step without purification. Yield, 70%.

Step 3

Preparation of Compound 9

Compound 8 (1 eq) and VS-PEG (266)—VS (HBVS, 40 eq, Catalog #22334, Pierce, Rockford, Ill.) were weighed in a 100 mL round bottom flask and DMF (10.0 mL, Catalog #354830025, Across Organics, Morris Plains, N.J.) was added. DIEA (2 eq, Catalog #387649-100 ml, Sigma Aldrich, St, Louis, Mo.) was added into the flask and the mixture was gently stirred (1000 rpm) at room temperature (24° C.) for ~8 hours. After 8 hours, the stirring was stopped.

Purification of Compound 9

The reaction mixture was purified by Sephadex LH-20 using DMF as eluent. Sephadex LH-20 medium gel filtration media (Catalog #17-0090-01, VWR International, Pittsburgh, Pa.) was soaked in DMF (25 mg/500 mL, Catalog #354830025, Across Organics, Morris Plains, N.J.) at room temperature (25° C.) for 24 hours. The presoaked Sephadex was loaded on to the glass column. The reaction mixture (10×1.0 mL) was loaded onto the column and eluted using DMF. The collected DMF fractions were poured dropwise into pre-cooled diethyl ether (60 ml) to precipitate the product. The product was dried under argon gas. Yield. 81%.

Step 4

Preparation of Compound 10

Compound 9 (0.059 g) was weighed in a 100 mL round bottom flask and hydrazine (3% in DMF; Catalog #303400-5G, Sigma Aldrich, St. Louis, Mo.) was added into the flask. The reaction mixture was gently stirred at (1000 rpm) at room temperature (24° C.) for ~3 hours. After 3 hours, the stirring was stopped.

Purification of Compound 10

Figure 11:
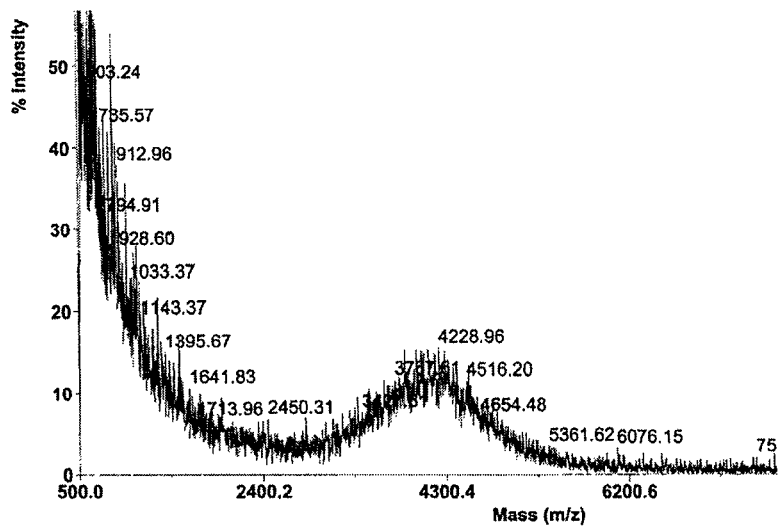
FIG. 11. MALDI-TOF mass spectrum of GABA-EMXL (compound 10).

The reaction mixture was purified by Sephadex LH-20 using DMF as eluent. Sephadex LH-20 medium gel filtration media (Catalog #17-0090-01, VWR International, Pittsburgh, Pa.) was soaked in DMF (25 mg/500 ml, Catalog #354830025, Organics, Morris Plains, N.J.) at room temperature (25° C.) for 24 hours. The presoaked Sephadex was loaded on to the glass column and the reaction mixture (10×1.0 mL) was loaded onto the column and eluted using DMF. The collected DMF fractions were poured dropwise into pre-cooled diethyl ether (60 ml) to precipitate the product. The product was dried under argon gas. Yield, 70%. The product was characterized by MALDI-TOF-MS (FIG. 11).

EXAMPLE 3

Synthesis of Biodegradable Crosslinker rEMXL

The biodegradable crosslinker rEMXL (containing thiol terminal) was prepared using $NH_2$-PEG—$NH_2$ (DAP, MW ~3350 Da), Dde-Glu-(γCOOH)-Cys(StBu)—$CONH_2$ [$R_1$] [Dde-GABA-$R_1$-SStBu] was coupled with diamino-PEG from both sides in DMF to obtain (Dde-$R_1$-SStBu)$_2$ PEG. The -StBu protecting group presets in $R_1$ were removed by treatment with DTT to introduce SH moieties on the two termini (FIG. 12).

Synthesis of rEMXL

Step 1 and 2

Steps 1 and 2 in this example follow the same procedure as set forth above in Example 1

Step 3

Preparation of rEMXL Crosslinker

Compound 3 (0.059 g) was weighed in a 100 mL round bottom flask and hydrazine (3% in DMF, Catalog #303400-5G, Sigma Aldrich, St. Louis, Mo.) was added into the flask. The reaction mixture was gently stirred (1000 rpm) at room temperature (24° C.) for ~3 hours. After 3 hours, the stirring was stopped.

Purification of rEMXL Crosslinker

The reaction mixture was purified by Sephadex LH-20 using DMF as eluent. Sephadex LH-20 medium gel filtration media (Catalog #17-0090-01, VWR international, Pittsburgh, Pa.) was soaked in DMF (25 mg/500 mL. Catalog #354830025, Across Organics, Morris Plains, N.J.) at room temperature (25° C.) for 24 hours. The presoaked Sephadex was loaded on to the glass column and reaction mixture (10×1.0 mL) was loaded onto the column and eluted using DMF. The collected DMF fractions were poured dropwise into pre-cooled diethyl ether (60 ml) to precipitate the product. The product was dried under argon gas. Yield. 70%.

EXAMPLE 4

Biodegradable Hydrogel Preparation Using Thiol-containing Copolymer and EMXL Crosslinker Preparation of Sodium Phosphate Buffer (0.02 M, pH=7.44±0.05)

Sodium phosphate dibasic (1 M, Catalog #S-9763, Sigma Aldrich, St. Louis, Mo.) and monobasic (1 M, Catalog #S-0751, Sigma Aldrich, St, Louis, Mo.) solutions were prepared separately in volumetric flasks. 1.54 mL of sodium phosphate dibasic and 0.46 mL of sodium phosphate monobasic solutions were transferred to a beaker and 80.0 mL of DI water was added to it. The pH of buffer was measured on a pH meter and pH value was adjusted to 7.44 using 0.1N sodium hydroxide solution (Catalog #SS276-4, Fisher Scientific, Suwanee, Ga.). The solution was transferred to a volumetric flask and more DI water was added to adjust the final volume to 100 mL. Unless otherwise indicated, all reference to DI refers to deionized water. Likewise, unless otherwise indicated, all reference to PB in example 3B refers to 0.02 M phosphate buffer, pH, 7.44.

Preparation of Polymer Solution Containing the Nanocarrier

Copolymer (4% w/v) was weighed in a centrifuge tube and dissolved in PB (132.8 μL).

Preparation of Crosslinker Solution

An EMXL crosslinker solution was prepared by weighing 4.8 mg of EMXL crosslinker in a centrifuge tube. PB (67.2 μL) was added to the centrifuge tube and the mixture vortexed for 2-3 minutes to dissolve the crosslinker into the buffer solution.

Preparation of Hydrogel (0.2 mL)

The copolymer solution (132.8 μL) was transferred to a glass vial (12×32 mm, SepCap clear vial, Catalog #C4011-80. National Scientific Company, Rockwood, Tenn.) followed by the crosslinker solution (67.2 μL). The solution mixture was allowed to stand at room temperature (24° C.). The hydrogel solution started becoming more viscous and formed the hydrogel in 1 min.

EXAMPLE 5

Biodegradable Hydrogel Preparation Using Thiol-containing Copolymer and GABAEMXL Crosslinker Preparation of Sodium Phosphate Buffer (pH=7.44±0.05)

The procedure for the preparation of phosphate buffer as set forth in Example 4 was used.

Preparation of Polymer Solution Containing the Nanocarrier

Copolymer (4% w/v) as weighed in a centrifuge tube and dissolved in PB (132.8 µL).

Preparation of Crosslinker Solution

The GABA-EMXL crosslinker solution was prepared by weighing 5.4 mg of GABA-EMXL crosslinker in a centrifuge tube. PB (67.2 µL) was added to the centrifuge tube and the mixture vortexed for 2-3 minutes to dissolve the crosslinker into the buffer solution.

Preparation of Hydrogel (0.2 mL)

The copolymer solution (132.8 µL) was transferred to a glass vial (12×32 mm, SepCap clear vial, Catalog #C4011-80, National Scientific Company, Rockwood, Tenn.) followed by the crosslinker solution (67.2 µL). The solution mixture was allowed to stand at room temperature (24° C.). The hydrogel solution started becoming more viscous and formed hydrogel in 1 min, 20 sec.

EXAMPLE 6

Non-degradable Hydrogel Preparation Using PEG-thiol Polymer and Vinyl Sulfone (VS)-containing INTGABAEMXL Crosslinker Preparation of Sodium Phosphate Buffer (pH=7.44±0.05)

The phosphate buffer was prepared as set forth above in Example 4.

Preparation of Polymer Solution Containing the Nanocarrier

8-Arm PEG thiol polymer (i.e., —SH side chain groups. 4% w/v) was weighed in a centrifuge tube and dissolved in PB (132.8 µL).

Preparation of Crosslinker Solution

Dde protected INTGABAEMXL (compound 9) crosslinker (i.e. VS groups) was prepared by weighing 4.8 mg of GABA-EMXL crosslinker in a centrifuge tube. PB (67.2 µL) was added to the centrifuge tube and the mixture vortexed for 2-3 minutes to dissolve the crosslinker into the buffer solution.

Preparation of Hydrogel (0.2 mL)

The polymer solution (132.8 µL) was transferred to a glass vial (12×32 mm, SepCap clear vial, Catalog #C4011-80, National Scientific Company, Rockwood, Tenn.) followed by the crosslinker solution (67.2 µL). The solution mixture was allowed to stand at room temperature (24'C). The hydrogel solution started becoming more viscous and formed a hydrogel in 1 min.

EXAMPLE 7

Non-degradable Hydrogel Preparation Using PEG-thiol Polymer and Vinyl Sulfone (VS)-containing INTEMXL Crosslinkers Preparation of Sodium Phosphate Buffer (pH=7.44±0.05)

The phosphate buffer was prepared as set forth above in Example 4.

Preparation of Polymer Solution Containing the Nanocarrier

8-Arm PEG thiol polymer (i.e., —SH side chain groups, 4% w/v) was weighed in a centrifuge tube and dissolved in PB (132.8 µL).

Preparation of Crosslinker Solution

Dde protected crosslinker INTEMXL (compound 4, i.e., VS groups) was prepared by weighing 4.8 mg of GABA-EMXL crosslinker in a centrifuge tube. PB (67.2 µL) was added to the centrifuge tube and the mixture was vortexed for 2-3 minutes to dissolve the crosslinker into the buffer solution.

Preparation of Hydrogel (0.2 mL)

The polymer solution (132.8 µL) was transferred to a glass vial (12×32 mm, SepCap clear vial, Catalog #C4011-80, National Scientific Company, Rockwood, Tenn.) followed by the crosslinker solution (67.2 µL). The solution mixture was allowed to stand at room temperature (24'C.). The hydrogel solution started becoming more viscous and formed hydrogel in 1 min.

EXAMPLE 8

Non-degradable Hydrogel Preparation Using Thiol-containing Copolymer and HBVS Crosslinker Preparation of Sodium Phosphate Buffer (pH=7.44±0.05)

The procedure for the preparation of phosphate butter was prepared as set forth above in Example 4.

Preparation of Polymer Solution Containing the Nanocarrier

The copolymer (4% w/v) was weighed in a centrifuge tube and dissolved in PB (132.8 µL)

Preparation of Crosslinker Solution

HBVS crosslinker solution was prepared by weighing 0.63 mg of HBVS crosslinker in a centrifuge tube. PB (67.2 µL) was added to the centrifuge tube and the mixture vortexed for 2-3 minutes to dissolve the crosslinker into the buffer solution.

Preparation of Hydrogel (0.2 mL)

The copolymer solution (132.8 µL) was transferred to a glass vial (12×32 mm, SepCap clear vial, Catalog #C4011-80, National Scientific Company, Rockwood, Tenn.) followed by the crosslinker solution (67.2 µL). The solution mixture was allowed to stand at room temperature (24° C.). The hydrogel solution started becoming more viscous and formed hydrogel in 1 min.

EXAMPLE 9

Non-degradable Hydrogel Preparation Using PEG-thiol Polymer and HBVS Crosslinker Preparation of Sodium Phosphate Buffer (pH=7.44±0.05)

The procedure for the preparation of phosphate buffer was prepared as set forth above in Example 4.

Preparation of Polymer Solution Containing the Nanocarrier

8-Arm PEG thiol polymer (i.e., SH termini, 4% w/v) was weighed in a centrifuge tube and dissolved in PB (132.8 µL).

Preparation of Crosslinker Solution

HBVS crosslinker solution was prepared by weighing 0.63 mg of HBVS crosslinker in a centrifuge tube. PB (67.2 µL) was added to the centrifuge tube and the mixture was vortexed for 2-3 minutes to dissolve the crosslinker into the buffer solution.

Preparation of Hydrogel (0.2 mL)

The polymer solution (132.8 µL) was transferred to a glass vial (12×32 mm, SepCap clear vial, Catalog #C4011-80, National. Scientific Company, Rockwood, Tenn.) followed by the crosslinker solution (67.2 µL). The solution mixture was allowed to stand at room temperature (24° C.). The hydrogel solution started becoming more viscous and formed hydrogel in 15 min.

EXAMPLE 10

Non-degradable Hydrogel Preparation Using PEG-thiol Polymer and Maleimide-containing BM[PEO]$_3$ Crosslinker Preparation of Sodium Phosphate Buffer (pH=7.44±0.05)

The procedure for the preparation of phosphate buffer (0.02 M) was prepared as set forth above in Example 4.

Preparation of Polymer Solution Containing the Nanocarrier

8-Arm PEG thiol polymer (i.e., SH termini, 4% w/v) was weighed in a centrifuge tube and dissolved in PB (132.8 µL).

Preparation Crosslinker Solution

BM [PEO]$_3$ crosslinker (i.e., maleimide groups) solution was prepared by weighing 0.5 mg of BM[PEO]$_3$ crosslinker in a centrifuge tube. PB (67.2 µL) was added to the centrifuge tube and the mixture was vortexed for 2-3 minutes to dissolve the crosslinker into the buffer solution.

Preparation of Hydrogel (0.2 mL)

The polymer solution (132.8 µL) was transferred to a glass vial (12×32 mm, SepCap clear vial, Catalog #C4011-80, National Scientific Company, Rockwood, Tenn.) followed by the crosslinker solution (67.2 µL). The solution mixture was allowed to stand at room temperature (24° C.). The hydrogel solution started becoming more viscous and formed the hydrogel in 1 min.

EXAMPLE 11

Non-degradable Hydrogel Preparation Using PEG-thiol Polymer and PEG Maleimide (5 kDa) Crosslinker Preparation of Sodium Phosphate Buffer (0.02 M, pH 7.44±0.05)

The procedure for the preparation of phosphate buffer was prepared as set forth above in Example 4.

Preparation of Polymer Solution Containing the Nanocarrier

8-Arm PEG thiol polymer (i.e. SH termini, 4% w/v) was weighed in a centrifuge tube and dissolved in PB (132.8 µL).

Preparation of Crosslinker Solution

5K PEG-maleimide crosslinker (i.e. maleimide groups) solution was prepared by weighing 0.5 mg of PEG-maleimide crosslinker in a centrifuge tube. PB (67.2 µL) was added to the centrifuge tube and the mixture was vortexed for 2-3 minutes to dissolve the crosslinker into the buffer solution.

Preparation of Hydrogel (0.2 mL)

The polymer solution (132.8 µL) was transferred to a glass vial (12×32 mm, SepCap clear vial, Catalog #C4011-80, National Scientific Company, Rockwood, Tenn.) followed by the crosslinker solution (67.2 µL). The solution mixture was allowed to stand at room temperature (24° C.). The hydrogel solution started becoming more viscous and formed hydrogel in 1 min.

EXAMPLE 12

Biodegradable Hydrogel Preparation Using Thiol-containing Copolymer and EMXL Crosslinker with Passively Entrapped FITC-Dextran (20 kDa)

Preparation of Sodium Phosphate Buffer (0.02 M, pH=7.44±0.05)

The procedure for the preparation of phosphate buffer was prepared as set above in Example 4.

Preparation of Polymer Solution Containing the Nanocarrier

Copolymer (4% w/v) was weighed in a centrifuge tube and dissolved in PB (132.8 µL).

Preparation of Crosslinker Solution

EMXL crosslinker solution was prepared by weighing 4.8 mg of EMXL crosslinker in a centrifuge tube, PB (67.2 µL) was added to the centrifuge tube and the mixture was vortexed for 2-3 minutes to dissolve the crosslinker into the buffer solution. The FITC-Dextran (20 kDa, 2 mg, Catalog #FD20, Sigma Aldrich, St, Louis, Mo.) was added to this solution and vortexed (<1 minutes) to make a clear solution.

Preparation of Hydrogel (0.2 mL)

The copolymer solution (132.8 µL) was transferred to a glass vial (12×32 mm, SepCap clear vial, Catalog #C4011-80, National Scientific Company, Rockwood, Tenn.) followed by the crosslinker solution (67.2 µL). The solution mixture was allowed to stand at room temperature (24° C.). The hydrogel solution started becoming more viscous and formed hydrogel in 1 min.

EXAMPLE 13

Biodegradable Hydrogel Preparation Using Thiol-containing Copolymer and EMXL Crosslinker with Passively Entrapped PEG(5 kDa)-Leu-Gly-Dox Preparation of Sodium Phosphate Buffer (0.02 M, pH=7.44±0.05)

The procedure for the preparation of phosphate buffer was prepared as set forth above in Example 4.

Preparation of Polymer Solution Containing the Nanocarrier

Copolymer (4% w/v)) was weighed in a centrifuge tube and dissolved in PB (132.8 µL).

Preparation of Crosslinker Solution

EMXL crosslinker solution was prepared by weighing 4.8 mg of EMXL crosslinker in a centrifuge tube. PB (67.2 µL) was added to the centrifuge tube and the mixture was vortexed for 2-3 minutes to dissolve the crosslinker into the buffer solution. The PEG(5 kDa)-Len-Gly-Dox (2 mg) was added to this solution and vortexed (<1 minutes) to make a clear solution.

Preparation of Hydrogel (0.2 mL)

The copolymer solution (132.8 µL) was transferred to a glass vial (12×32 mm, SepCap clear vial, Catalog #C4011-80, National Scientific Company. Rockwood, Tenn.) followed by the crosslinker solution (67.2 µL). The solution mixture was allowed to stand at room temperature (24° C.). The hydrogel solution started becoming more viscous and formed hydrogel in 1 min.

EXAMPLE 14

In Vitro Release of Passively Entrapped FITC-Dextran (Model Drug) in PBS from Biodegradable Hydrogels Prepared Using Copolymer and EMXL Crosslinker Preparation of Sodium Phosphate Buffered Saline (0.1M, pH=7.44±0.05)

Sodium chloride (8 gm, Catalog #SX0420-3, EM Sciences, Gibbstown, N.J.), Potassium chloride (0.2 gm, Catalog #BP360-1, Fisher Scientific, Fair Lawn, N.J.), sodium phosphate dibasic (1.44 gm, Catalog #S-9763, Sigma Aldrich, St. Louis, Mo.) and potassium phosphate monobasic (0.24 gm Catalog #P285, Fisher Scientific, Fair Lawn, N.J.) were transferred to a volumetric flask (1 liter), 800 ml of DI water was added to it. The pH of buffer was adjusted to 7.44 using 1N sodium hydroxide solution (Catalog #SS276-4, Fisher Scientific, Fair Lawn, N.J.) or 1N hydrochloric acid solution (Catalog #920-1, Sigma Aldrich, St. Louis, Mo.). The solution was transferred to a volumetric flask and more DI water was added to adjust the final volume to 1000 mL.

FITC-Dextran (Model Drug) Release

Release of FITC-Dextran from EMXL hydrogel depots was studied at 37° C. in PBS. FITC-Dextran was loaded into the hydrogels by mixing, it with an aqueous solution of copolymer and crosslinker. The release of physically entrapped FITC-Dextran from hydrogel depot was studied and analyzed by florescence. Water-soluble degradable FITC-Dextran (20 kDa, 2 mg, Catalog #FD20, Sigma Aldrich, St, Louis, Mo.) loaded hydrogels were prepared (200 µL) using 4% w/v copolymer and EMXL crosslinker. After equilibration, the hydrogels were transferred to flat bottom vials (12×32 mm, SepCap clear vial, Catalog #C4011-80, National Scientific Company, Rockwood, Tenn.) and completely submerged in 500 µL PBS. Aliquots 500 µL were withdrawn at regular time intervals and replenished with equal amounts of fresh PBS. The concentration of FITC-Dextran in release samples was determined using a plate reader with an excitation wavelength of 490 nm and emission wavelength of 510 nm. The release profile suggested a typical diffusion-controlled release of a FITC-Dextran from the hydrogel 99% FITC-Dextran was released in 29.5 h.

EXAMPLE 15

In Vitro Release of Passively Entrapped FITC-Dextran (Model Drug) in PBS from Biodegradable Hydrogels Prepared Using Copolymer and GABA-EMXL Crosslinker Preparation of Sodium Phosphate Buffer Saline (pH=7.44±0.05)

The procedure for the preparation of PBS is set forth above in Example 14.

FITC-Dextran (Model Drug) Release

Release of FITC-Dextran from GABA-EMXL hydrogel depots was studied at 37° C. in PBS according to the procedure set forth above in Example 14. The release profile suggested a typical diffusion-controlled release of a FITC-Dextran from the hydrogel, as observed in example 14. FITC-Dextran (99%) was released in 17.5 h.

EXAMPLE 16

In Vitro Release of Passively Entrapped FITC-Dextran (Model Drug) in Mouse Plasma from Biodegradable Hydrogels Prepared Using Copolymer and EMXL Crosslinker Release of FITC-Dextran from the hydrogel depots was studied at 37° C. in mouse plasma. FITC-Dextran was loaded into the hydrogels by mixing it with an aqueous solution of copolymer and cross-linker as described above according to the procedure in Example 15 and 16.

The release of physically trapped FITC-Dextran (20 kDa) from the hydrogel depot was studied and analyzed by florescence, Water-soluble degradable FITC-Dextran (20 kDa, 2 mg, Catalog FD20, Sigma Aldrich, St. Louis, Mo.) loaded hydrogels were prepared (200 µL) using copolymer (4% w/v) and EMXL crosslinkers. After equilibration, the hydrogels were transferred to flat bottom vials (12×32 mm, SepCap clear vial, Catalog #C4011-80, National Scientific Company, Rockwood, Tenn.) and completely submerged in 500 µL mouse plasma. Aliquots 500 µL (mouse plasma) were withdrawn at regular time intervals and replenished with same amounts of fresh mouse plasma. The concentration of FITC-Dextran in release samples was determined using a plate reader with an excitation wavelength of 490 nm and emission wavelength of 510 nm. The release profile suggests a typical diffusion-controlled release of a FITC-Dextran from the hydrogel; 99% of FITC-Dextran was released by 47 h.

EXAMPLE 17

In Vitro Release of Passively Entrapped FITC-Dextran (Model Drug) in Mouse Plasma Front Biodegradable Hydrogel Prepared Using Copolymer and GABA-EMXL Crosslinker Release of FITC-Dextran from hydrogel depots was studied at 37° C. as described in example 16. FITC-Dextran was loaded into the hydrogels by mixing it with an aqueous solution of copolymer (4%, w/v) and GABA-EMXL crosslinker.

The release studies were carried by following the procedure described above as set forth in Example 16. The release profile suggested a typical diffusion-controlled release of a FITC-Dextran and about 98% of the compound was released in 72 h.

EXAMPLE 18

In Vitro Degradation Studies in PBS of Biodegradable Hydrogels Prepared Using Copolymer and EMXL Crosslinker Preparation of Sodium Phosphate Buffered Saline (PBS; pH pH=7.44±0.05)

The procedure for the preparation of PBS was used as set forth above in Example 14.

Hydrogel Degradation Studies

Hydrogel (200 µL) were prepared using copolymer (4% w/v) and EMXL crosslinker. After the equilibration, the hydrogels were transferred to flat bottom vials (12×32 mm, SepCap clear vial, Catalog #C4011-80, National Scientific Company, Rockwood, Tenn.). Hydrogels were exposed to PBS (500 µL) and incubated at 37° C. Aliquots (500 µL) were taken at regular time intervals and replaced with fresh PBS. Hydrogel degradation occurs because the free amino group of Glu (EMXL cross-linker) attacks the γ-carboxylic group of the same molecule and as a result the two γ-amide bonds between the Glu and PEG break, releasing the DAP in solution (FIG. 6). Since DAP is a non-fluorescent molecule; a fluorescamine assay[24] was performed to measure the hydrogel degradation by measuring the amine present in solution. Hydrogels were found to biodegrade in 29.5 h at 37° C.

EXAMPLE 19

In Vitro Degradation Studies in PBS of Biodegradable Hydrogels Prepared Using Copolymer and GABA-EMXL Crosslinker Preparation of Sodium Phosphate Buffered Saline (PBS; pH=7.44±0.05)

The procedure for the preparation of PBS was used as set forth above in Example 14.

Hydrogel Degradation Studies

Hydrogel (200 μL) were prepared using copolymer (4%, w/v) and GABA-EMXL crosslinker. The degradation studies were carried out according to the procedure described above in Example 18. Hydrogel degradation occurs because the free amino group of GABA (GABA-EMXL cross-linker) attacks the γ-carboxylic group of the same molecule and as a result the two γ-amide bonds between the Glu and PEG break, releasing the DAP in solution (FIG. 6). The fluorescamine assay[24] used to measure DAP in solution showed that these hydrogels biodegrade (100%) in 10 h at 37° C. released

EXAMPLE 20

In Vitro Degradation Studies in Mouse Plasma of Biodegradable Hydrogels Prepared Using Copolymer and EMXL Crosslinker Hydrogels (200 μL) were prepared using copolymer (4%, w/v) and EMXL crosslinker. After the equilibration, the hydrogels were transferred to flat bottom vials (12×32 mm, SepCap clear vial, Catalog #C4011-80, National Scientific Company, Rockwood, Tenn.) and exposed to mouse plasma (500 μL, pH=7.4). Samples were incubated at 37° C. and aliquots (500 μL) were taken at regular time intervals and replaced with same amount of mouse plasma. The fluorescamine assay[24] was used to measure the free amine present in solution and it was estimated that hydrogels biodegrade in 360 h at 37° C.

EXAMPLE 21

In Vitro Degradation Studies in Mouse Plasma of Biodegradable Hydrogels Prepared Using Copolymer and GABA-EMXL Crosslinker Hydrogels (200 μL) were prepared using copolymer (4%, w/v) and GABA-EMXL crosslinker. The biodegradation studies were carried out according to the procedure set forth above in Example 20. Fluorescamine assay[23] for free amine (DAP) showed that hydrogels biodegrade at 37° C. in 119 h.

EXAMPLE 22

Biodegradation Studies in PBS Using Swelling Ratios for Hydrogels Prepared Using Copolymer and EMXL Crosslinker Preparation of Sodium Phosphate Buffer Saline (PBS; pH=7.44±0.05)

The procedure for the preparation of PBS was used as set forth above in Example 14.

Hydrogel Degradation Studies

Figure 14:
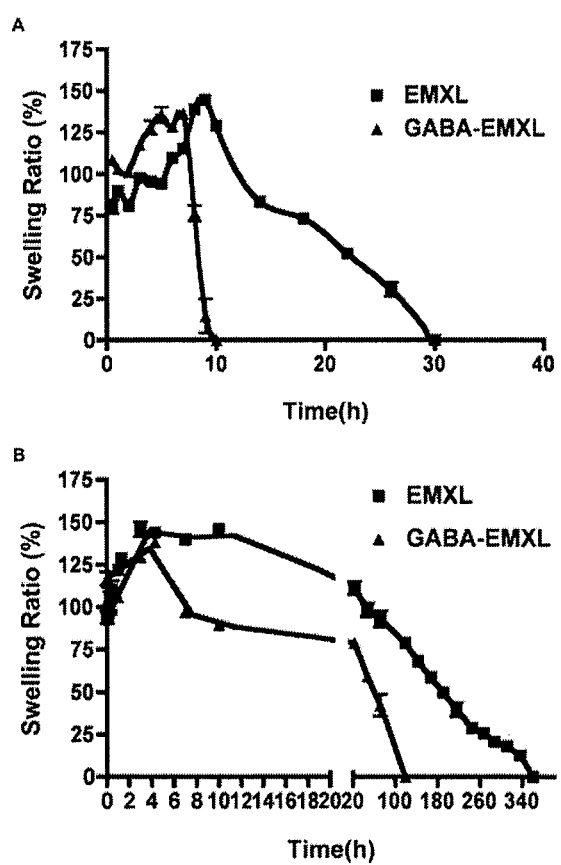
FIG. 14. Swelling ratio % ($W_1/W_0*100$) profile of EMXL and GABA-EMXL hydrogels in (A) PBS (pH 7.4) and (B) Mouse Plasma at 37° C. (average±S.D. n=3).

The hydrogels (200 μL) were prepared using copolymer (4%, w/v) and EMXL crosslinker and transferred to flat bottom vials (12×32 mm, SepCap clear vial, Catalog #C4011-80, National Scientific Company, Rockwood, Tenn.), PBS (500 μL) solution was applied on the hydrogels and hydrogels were incubated, at 37° C. The swollen hydrogels were weighed at regular time intervals after removal of the buffer. After each measurement the buffer was replenished. The hydrogel displayed gradual swelling at initial tnne, unttl they rapidly dissolved (FIG. 14). The hydrogels swelled in 8-10 h and biodegraded at 37° C. in 29.5 h.

EXAMPLE 23

Biodegradation Studies in PBS Using Swelling Ratios for Hydrogels Prepared Using Copolymer and GABA-EMXL Crosslinker Preparation of Sodium Phosphate Buffer Saline (PBS; pH=7.44±0.05)

The procedure for the preparation of PBS was used as set forth above in Example 14.

Hydrogel Degradation Studies

The hydrogels (200 μL) were prepared using copolymer (4%, w/v) and GABA-EMXL crosslinker. The swelling, studies were carded out according to the procedures set forth above in Example 22. Hydrogels swelled in 6-7 h and degraded in 10 h at 37° C. (FIG. 14).

EXAMPLE 24

Biodegradation Studies in Mouse Plasma Using Swelling Ratios for Hydrogels Prepared Using Copolymer and EMXL Crosslinker Hydrogels (200 μL) prepared using copolymer (4%, w/v) and EMXL crosslinker were transferred to flat bottom vials (12×32 mm, SepCap clear vial, Catalog #C4011-80, National Scientific. Company, Rockwood, Tenn.). Mouse plasma (500 μL) was applied and the hydrogels were incubated at 37° C. The swollen hydrogels were weighed at regular time intervals after removal of the mouse plasma. After each weighing the mouse plasma was replenished. The hydrogel displayed gradual swelling at initial time until they rapidly dissolved (FIG. 14). EMXL hydrogel swelled in 4-10 h and degraded in 360 h at 37° C.

EXAMPLE 25

Biodegradation Studies in Mouse Plasma Using Swelling Ratios for Hydrogels Prepared Using Copolymer and GABA-EMXL Crosslinker Hydrogels (200 μL) prepared using copolymer (4% w/v) and GABA-EMXL crosslinker were transferred to flat bottom vials and swelling studies were carried out according to the procedure set forth above in Example 24. Hydrogels swelled in 2-4 h and degraded in 119 h at 37° C. in mouse plasma (FIG. 14).

EXAMPLE 26

Synthesis of Biodegradable PEG-Glu($NH_2$)(γ)-Lys(Z)OMe Conjugates

Fmoc-Glu-(γCOOtBu)—COOH was coupled to amino-PEG (20 kDa) in DMF to obtain Frnoc-Glu-(γCOOtBu)-CONHPEG. The free —COOH group was reacted with H-Lys(Z)-OMe to obtained PEG-Glu($NH_2$)(γ)-Lys(Z)OMe conjugates FIG. 15)

Synthesis PEG-Glu($NH_2$)(γ)-Lys(Z)Ome

Step 1

Preparation of Compound 13

The Fmoc-Glu-(γCOOtBtu)—COOH (7 eq, Catalog #04-12-1020, Novabiochem, San Diego, Calif., USA), PEG—$NH_2$ (20 kDa, 7 eq, Catalog #Sunbright GL2-200PA, NOF Corporation, White Plains, N.Y.), and PyBOP (7 eq, Catalog

01-62-0016, Novabiochem, San Diego, Calif., USA) were weighed in a 100 mL round bottom flask and DCM (10.0 mL, Catalog D150-4, Fisher Scientific Suwanee, Ga., USA) was added. DIEA (0.0118 ml, 4 eq. Catalog #387649-1.00 ml, Sigma Aldrich, St. Louis, Mo. 63178, USA) was added into the flask and the mixture was gently stirred at (1000 rpm) at room temperature (24° C.) for ~8 hours. After 8 hours, the stirring was stopped.

Purification of Compound 13

The reaction mixture was purified by Sephadex G-50 using water as the eluent Sephadex G-50 medium gel filtration media (Catalog #17.0043-01, VWR International, Pittsburgh, Pa.) was soaked in DI water (25 mg/500 mL) at room temperature (25° C.) for 24 hours. The presoaked Sephadex was loaded on to the column. Reaction mixture (10×1.0 mL) was loaded onto the column and eluted using DI water. The collected fractions were lyophilized for 3-days. Yield. 80%.

Step 2

Preparation of Compound 14

The compound 13 (0.5 gm, 1 eq) was weighed in a 100 mL round bottom flask. 20% TFA (Catalog #61030/91709-1EA, Sigma Aldrich, St. Louis, Mo.) in DCM (10.0 mL) was added into the flask and the mixture was gently stirred at (1000 rpm) at room temperature (24° C.) for ~1 hours. After 1 hour, the stirring was stopped.

Purification of Compound 14

The purification procedure was used as mentioned in step 1 of this example Yield. 83%.

Step 3

Preparation of Compound 15

The compound 14 (0.120 g, 1 eq), Z-Lys-OMe (0.0195 g, 1 eq, Catalog #01-12-0607, Novabiochem, San Diego, Calif., USA) and PyBOP (7 eq, Catalog #01-62-0016, Novabiochem, San Diego, Calif., USA) were weighed in a 100 mL round bottom flask and DCM (10.0 mL, 10.0 mL, Catalog #D150-4, Fisher Scientific, Suwanee, Ga., USA) was added. DIEA (0.001088 ml, 1.4 eq, Catalog #387649-100, Sigma Aldrich, St. Louis, Mo. 63178, USA) was added into the flask and the mixture was gently stirred (1000 rpm) at room temperature (24° C.) for ~8 hours. After 8 hours, the stirring was stopped.

Purification of Compound 15

The purification procedure for the preparation was used as mentioned in step 1 of this example. Yield, 72%.

Step 4

Preparation of Compound 16

The compound 15 (0.200 g, 1 eq), was weighed in a 100 mL round bottom flask. Piperidine (10%, Catalog #104094 Sigma Aldrich, St. Louis, Mo.) in DCM (10.0 mL, Catalog #D150-4, Fisher Scientific, Suwanee, Ga., USA) was added into the flask and the mixture was gently stirred at (1000 rpm) at room temperature (24° C.) for ~0.5 hours. After 0.5 hours, the stirring as stopped.

Purification of Compound 16

The purification procedure was used as mentioned in step 1 of this example. Yield. 70%.

EXAMPLE 27

Synthesis of Biodegradable PEC-Glu(NH$_2$)(γ)-ZLys-OMe Conjugate

Figure 15:
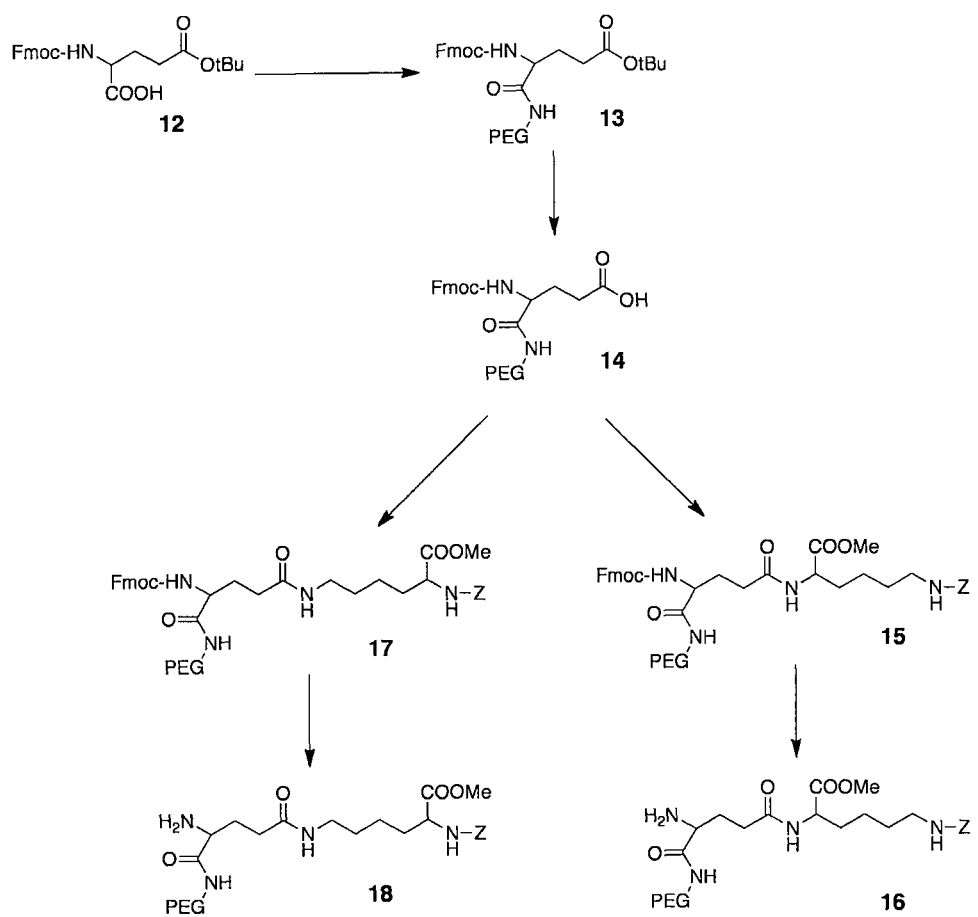
FIG. 15. Synthesis of PEG-Glu-(α)Lys(Z)OMe and PEG-Glu-(γ)Lys(Z)OMe conjugates, a) PEG—$NH_2$ (20 kDa), PyBOP, DIEA, DCM, 24° C., 8 h; b) 20% TFA in DCM, 24° C., 1 h; c) Z-LysOMe, PyBOP, DIEA, DCM, 24° C., 8 h, d) 10% pipyridine in DCM, 24° C. 0.5 h; e) H-Lys(Z)OMe, PyBOP, DIEA, DCM, 24° C., 8 h; f) 10% pipyridine in DCM, 24° C., 0.5 h.

Fmoc-Glu-(γCOOtBu)—COOH was coupled to amino-PEG (20 kDa) in DMF to obtain Fmoc-Glu-(γCOOtBu)-CONHPEG. The free —COOH group was reacted with Z-Lys-OMe to obtained PEG-Glu(NH$_2$)(γ)-(7)Lys-OMe conjugate (FIG. 15).

Step 1

Preparation of Compound 17

The compound 14 (0.120 g, 1 eq), H-Lys(Z)-OMe (0.0279 g, 4 eq, Catalog #04-12-5024, Novabiochem, San Diego, Calif., USA), and PyBOP (0.0439 g, 4 eq Catalog #01-62-0016, Novabiochem, San Diego, Calif., USA) were weighed in a 100 mL round bottom flask and DCM (10.0 mL, Catalog # D150-4, Fisher Scientific, Suwanee, Ga., USA) was added. DIEA (0.001088 ml, 1.4 eq, Catalog 387649-100, Sigma Aldrich, St. Louis, Mo.) was added into the flask and the mixture was gently stirred at (1000 rpm) at room temperature (24° C.) for ~8 hours. After 8 hours, the stirring was stopped.

Purification of Compound 17

The purification procedure was performed according to the procedure set forth above in step 1 of Example 26, Yield. 70%.

Step 4

Preparation of Compound 18

The compound 17 (0.200 g, 1 eq), was weighed in a 100 mL round bottom flask, Piperidine (10%, Catalog #104094, Sigma Aldrich, St, Louis, Mo.) in DCM (10 ml 10.0 mL, Catalog #D150-4, Fisher Scientific, Suwanee, Ga., USA) was added into the flask and the mixture was gently stirred at (1000 rpm) at room temperature (24° C.) for ~0.5 hours. After 0.5 hours, the stirring was stopped.

Purification of Compound 18

The purification procedure was performed according to the procedure set forth above in step 1 of example 26. Yield, 68%.

EXAMPLE 28

In vitro Release of Lys(Z)-OMe from PEG-Glu (NH$_2$)-(α)Lys(Z)-OMe Conjugate in PBS Preparation of Sodium Phosphate Buffer Saline (pH=7.44±0.05)

The procedure for the preparation of PBS was prepared according to the procedure set forth above in Example 14.

In Vivo Release of Lys(Z)OMe from PEG-Glu(NH$_2$)-(α) Lys(Z)OMe Conjugate

PEG-Glu(NH$_2$)-(α)Lys(Z)OMe conjugate (15 mg) was dissolved in PBS (15 ml) and incubated at 37° C. Aliquots (50 μL) were taken at regular time intervals and the sample aliquots were dried using a CentriVap (Labconco Corporation, Kansas City, Mo.). The cumulative cleavage (%) of Lys(Z) OMe from PEG-Glu(NH$_2$)-(α)Lys(Z)OMe conjugate was measured using fluorescamine assay[24]. The release studies showed that ~99% release occurs in 490 h.

EXAMPLE 29

In vitro Release of Z-Lys(COOH)OMe from PEG-Glu(NH$_2$)-(ε)Lys(Z)OMe Conjugate in PBS Preparation of Sodium Phosphate Buffer Saline (pH=7.44±0.05)

The procedure for the preparation of PBS was prepared according to the procedure set forth above Example 14.

Release of Lys(Z)Ome from PEG-Glu(NH$_2$)-(α)Lys(Z) OMe Conjugate

PEG-Glu(NH$_2$)-(ε)Lys(Z)OMe conjugates (15 mg) was dissolved in PBS (15 ml) and incubated at 7° C. Aliquots (50 μL) were taken at regular time intervals and the sample aliquots were dried using a CentriVap (Labconco Corporation, Kansas City, Mo.). The cumulative cleavage (%) of Z-LysOMe from PEG-Glu(NH$_2$)-(ε)Lys(Z)OMe conjugate was measured using fluorescamine assay[24]. The release studies showed that 99% of Z-LysOMe was released from PEG-Glu(NH$_2$)-($\epsilon$)Lys(Z)OMe conjugates in ~29 h.

EXAMPLE 30

Figure 16:
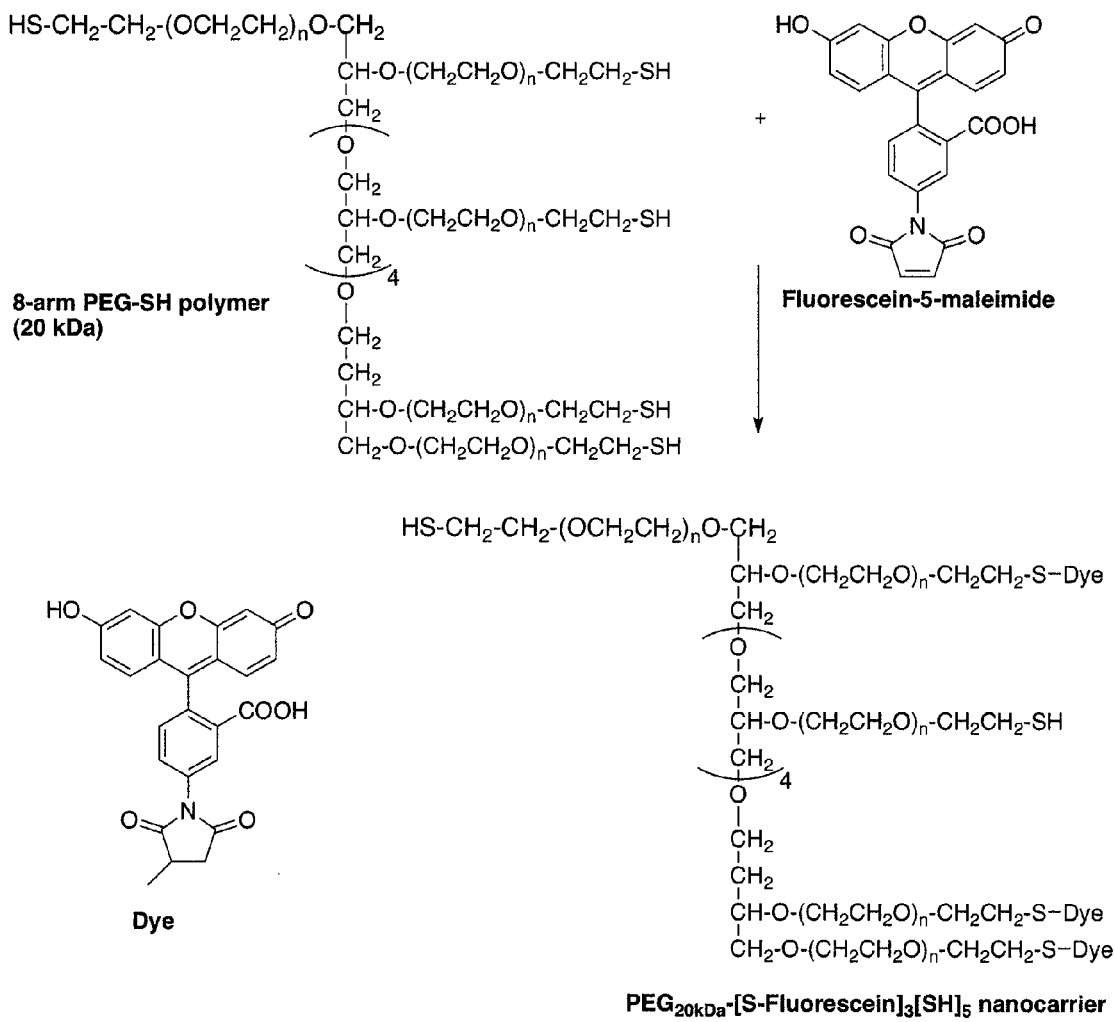
FIG. 16. Synthesis of $PEG_{20kDa}$-[S-fluorescein]$_3$[SH]$_5$ nanocarrier, Polymer was dissolved in sodium phosphate-EDTA buffer (0.1 M, pH=7.40) and fluorescein-5-maleimide dissolved in DMF was added to the polymer solution. Reaction mixture was stirred at room temperature for 12 h in dark.

Preparation of PEG$_{20KDa}$-[S-Fluorescein]$_3$[SH]$_5$ Nanocarrier to Obtain Crosslinked Nanocarrier Hydrogel (FIG. 16)
Preparation of Sodium Phosphate Buffer (0.1 M, pH=7.44±0.05) Containing Ethylene Diamine Tetraacetate (EDTA, 5 mM)
Sodium phosphate dibasic (1M Catalog #S-9763 Sigma Aldrich, St. Louis, Mo.) and sodium diphosphate monobasic solutions (1M, Catalog #S-0751, Sigma Aldrich, St. Louis, Mo.) were prepared in DI water. Sodium phosphate dibasic (7.74 mL) and sodium phosphate monobasic (2.26 ml) solutions were mixed into a beaker. DI water (80.0 mL) was added to the beaker and EDTA was dissolved (186.1 mg, Sigma Aldrich, St. Louis, Mo.) in it. The pH was measured on pH meter (Symphony B70P, VWR International, Pittsburgh, Pa.) and adjusted to 7.40 using 0.1 N sodium hydroxide solution (Catalog #SS276-4, Fisher Scientific, Suwanee, Ga.). The buffer was transferred to a volumetric flask and DI water was added to adjust the final buffer volume to 100 mL.
Preparation of Nanocarrier
the thiol-functionalized eight-arm poly(ethylene glycol) polymer (PEG$_{20kDa}$-[SH]$_8$, 100 mg, 4.65×10$^{-3}$ mM; Catalog #SUNBRIGHT HGEO-200SH, NOF America Corporation, White Plains, N.Y.) was weighed in a 50 mL centrifuge tube and PB (10.0 mL) was added. The mixture was gently stirred at (1000 rpm) at room temperature (24° C.) to obtain a clear solution, Fluorescein-5-maleimide (0.5 equiv., 5.17 mg; Catalog #81405, Anaspec, San Jose, Calif.) was dissolved in DMF (0.5 Catalog #EM-DX1727-6, VWR International, Pittsburgh, Pa.) and added to the polymer solution. The centrifuge tube containing the reaction mixture was covered with aluminum foil (to maintain dark conditions) and stirred at (1000-1500 rpm) at room temperature (24° C.) for overnight period (~12 hours). After 12 hours, the stirring was stopped.
Purification of Nanocarrier
The nanocarrier was purified by GPC on Sephadex G50 column in dark, using DI water as the eluent. The reaction mixture (10×1.0 mL) was loaded onto the column and eluted using DI water; the high molecular weight nanocarrier eluted first, followed by the low molecular weight free fluorescein. High molecular weight fractions were pooled together and lyophilized for 5-days (Labconco, FreeZone 2.5 plus, temperature: −84° C.; pressure: 0.010 millibar). Nanocarrier was obtained as yellow flakes (76.3 mg).
Characterization of Nanocarrier
The nanocarrier was characterized on Waters Breeze GPC system (Waters Corporation, Milford, Mass.). The unmodified polymer showed retention time of 8.9 minutes whereas the nanocarrier showed the retention time of 8.0 minutes. The unmodified polymer showed a peak in refractive index panel but not the UV panel because PEG does not absorb at 480 nm, however, nanocarrier showed peak in UV panel too due to the presence of fluorescein, which strongly absorbs at 480 nm wavelengths.
Different nanocarrier examples are summarized in Table 1.

TABLE 1

| Nanocarrier | Polymer | Dye | Yield (mg) |
|---|---|---|---|
| PEG$_{20\,kDa}$-[S-fluorescein]$_3$[SH]$_5$ | PEG$_{20\,kDa}$-[SH]$_8$ | Fluorescein-5-maleimide (3 equiv.) | 76.3 |

TABLE 1-continued

| Nanocarrier | Polymer | Dye | Yield (mg) |
|---|---|---|---|
| PEG$_{20\,kDa}$-[S-fluorescein]$_1$[SH]$_7$ * | PEG$_{20\,kDa}$-[SH]$_8$ | Fluorescein-5-maleimide (1 equiv.) | 84.2 |
| PEG$_{20\,kDa}$-[S-fluorescein]$_{0.5}$[SH]$_{7.5}$ * | PEG$_{20\,kDa}$-[SH]$_8$ | Fluorescein-5-maleimide (0.5 equiv.) | 84.0 |
| PEG$_{20\,kDa}$-[S-methylene blue]$_1$[SH]$_7$ * | PEG$_{20\,kDa}$-[SH]$_8$ | Methylene blue maleimide (1 equiv.) | 69.1 mg |

* Nanocarriers prepared using the procedure described in example 30. Methylene blue maleimide was obtained from ATTO-TEC GmbH, Siegen, Germany (Catalog # AD MB-2-45).

EXAMPLE 31

Preparation of Biodegradable Hydrogels using PEG$_{20kDa}$-[S-Fluorescein]$_{0.5}$[SH]$_{7.5}$ Nanocarrier and PEG$_{3.4kDa}$-[NHS]$_2$ Crosslinker Preparation of Sodium Phosphate Buffer (0.02 M, pH=7.44±0.05)
Sodium phosphate dibasic (1M. Catalog #S-9763, Sigma Aldrich, St. Louis, Mo.) and monobasic (1M, Catalog #S-0751, Sigma Aldrich, St. Louis, Mo.) solutions were prepared separately in volumetric flasks. Sodium phosphate dibasic (1.54 mL) and monobasic (0.46 mL) solutions were transferred to a beaker and 80.0 mL of DI water was added to it. The pH of buffer was measured according to the procedures set forth above in Example 30 and adjusted to 7.44 using. 0.1N sodium hydroxide solution (Catalog # SS276-4, Fisher Scientific, Suwanee, Ga.). The solution was transferred to a volumetric flask and more DI water was added to adjust the final volume to 100 mL.
Preparation of Nanocarrier Solution
PEG$_{20kDa}$-[S-fluorescein]$_{0.5}$[SH]$_{7.5}$ nanocarrier (4 mg, 2×10$^{-4}$ mM) was weighed in a centrifuge tube and PB (0.8 mL) was added. The solution was briefly (~1-2 min) vortexed to make a clear solution.
Preparation of Crosslinker Solution
Crosslinker solution was prepared by weighing PEG$_{3.4kDa}$-[NHS]$_2$ crosslinker (4 equiv., 8×10$^{-4}$ mM, Catalog # SUNBRIGHT DE-034GS, NOF America, White Plains, N.Y.) in a centrifuge tube and dissolving it into PB (0.2 mL).
Preparation of Hydrogel (1.0 mL)
The nanocarrier solution (0.8 mL) was transferred to a glass vial (12×32 mm, SepCap clear vial, Catalog #C4011-80, National Scientific Company, Rockwood, Tenn.) followed by the crosslinker solution (0.2 mL). The solution mixture was allowed to stand at room temperature (24° C.). The solution started becoming, more and more viscous and ceased to flow from the inverted tube in 16 min indicating the hydrogel formation.
Hydrogel examples prepared using thioester bonds are summarized in Table 2.

TABLE 2*

| Nanocarrier | Crosslinker | Time (min) taken for hydrogel formation |
|---|---|---|
| PEG$_{20\,kDa}$-[S-fluorescein]$_{0.5}$[SH]$_{7.5}$ (4%, w/v) | PEG$_{3.4\,kDa}$-[NHS]$_2$ (4 equiv.) | 16 |

TABLE 2*-continued

| Nanocarrier | Crosslinker | Time (min) taken for hydrogel formation |
|---|---|---|
| $PEG_{20\,kDa}$-[S-fluorescein]$_{0.5}$[SH]$_{7.5}$ (4%, w/v) | $PEG_{3.4\,kDa}$-[NHS]$_2$ (8 equiv.) | 05 |
| $PEG_{20\,kDa}$-[S-fluorescein]$_{0.5}$[SH]$_{7.5}$ (6%, w/v) | $PEG_{3.4\,kDa}$-[NHS]$_2$ (4 equiv.) | 06 |

Proof of principle work. Hydrogels prepared using degradable thioester bonds and elimination mechanism based crosslinkers for timed biodegradation were not used. All hydrogels were prepared using the procedure described in example 31.

EXAMPLE 32

Figure 17:
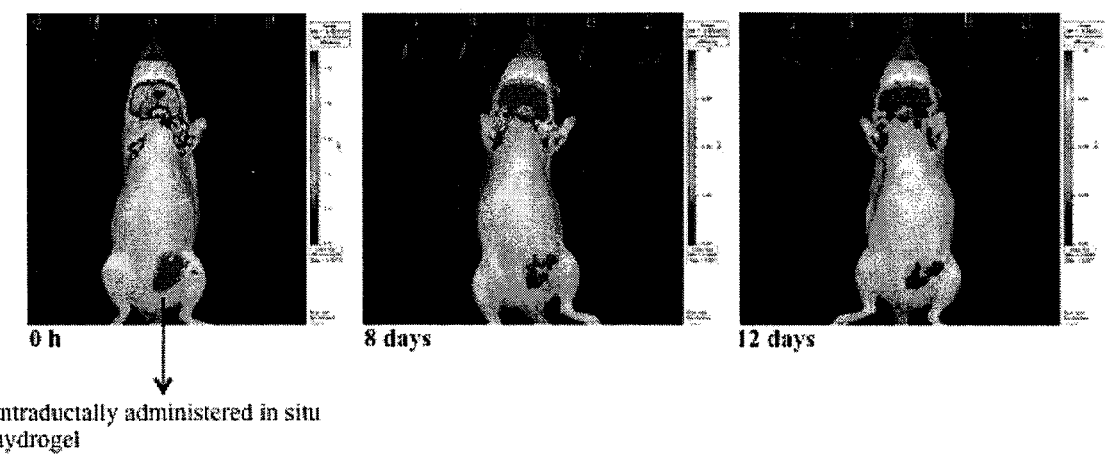
FIG. 17. Non-invasive retention studies of an in situ hydrogel in rats breast duct. Hydrogel (0.1 mL) were formed in situ in the breast duct by crosslinking of $PEG_{20kDa}$-[S-fluorescein]$_{0.5}$[SH]$_{7.5}$ nanocarrier with $PEG_{3.4kDa}$-[NHS]$_2$ crosslinker through thioester bonds.

Non-invasive Hydrogel Retention Studies in Rats Breast Duct (FIG. 17)

Animal

Six-weeks old, female Sprague-Dawley rats were obtained (Hilltop Lab Animals, Inc., Scottdale, Pa.) and housed in Rutgers Laboratory Animal Services facility accredited by Association for the Assessment and Accreditation of Laboratory and Care International (AAALAC). They were maintained on a 12-hour light/dark cycle and received laboratory chow and water ad libitum. Animals were housed three per cage and allowed to acclimatize at least 1-day prior to the studies. All experiments were carried out under established federal regulations and animal protocols (protocol # 05-026) approved by the Rutgers University Institutional Animal Care and Use Committee. A day prior to the study, the rat body was clipped with a clipper under anesthesia with isoflurane (AErrane, Catalog #NDC 10019-773-40, Baxter, Deerfield, Ill.) and Veet (Reckitt Benckiser North America, Parsippany, N.J.) was applied on the clipped skin Veet was removed 5 minutes post application and rats were washed with warm water and wiped with dry paper towels.

Preparation of Hydrogel Solution

The nanocarrier ($PEG$-$_{20kDa}$-[S-fluorescein]$_{0.5}$[SH]$_{7.5}$) solution was prepared in PB at a concentration of 4 mg/0.8 mL whereas the crosslinker solution ($PEG_{3.4kDa}$-[NHS]$_2$) was prepared at a concentration of 2.7 mg/0.2 mL. The nanocarrier and crosslinker solutions were mixed together in a centrifuge tube.

Intraductal Administration and in situ Hydrogel Formation

Rat under anesthesia with isoflurane (AErrane, Catalog #NDC 10019-773-40, Baxter, Deerfield, Ill.) was placed under a surgical microscope (Stereomaster, Fisher Scientific, Suwanee, Ga.) equipped with a ring lamp, and magnification was adjusted to operator's comfort to aid the injection procedure. The hydrogel solution (0.1 mL) prepared above was injected into the third teat (counting from the head) using a 33 G needle (Catalog #7747-01, Hamilton, Reno, Nev.) attached to a 0.1 ml Hamilton syringe (Catalog #81020, Hamilton, Reno, Nev.), them situ hydrogels (palpable) are formed in about ~16-20 minutes. The process was repeated with two more rats.

Non-invasive Hydrogel Retention in Rats

After the intraductal hydrogel administration, rats were immediately imaged (one at a time) on IVIS 100 optical imaging system (Xenogen Imaging Technologies, now part of Caliper Life Sciences, Hopkinton, Mass.). The system was set up as follows: Level: High; Em/Ex: GFP, Bin; HR (4); FOV 25; Aperture: f4; and Shutter: 1 s. The animals were then imaged at different time points. Fluorescent intensity of the injected area subtracted with that of uninjected distal area was used for hydrogel quantitation in ducts. Hydrogels prepared using degradable thioester bonds were retained in ducts for 30-days.

*Proof of principle work. Hydrogels prepared using degradable thioester bonds and elimination mechanism based crosslinkers for timed biodegradation were not used.

EXAMPLE 33

EMXL-hydrogel Degradation Studies in Mice

Animal

Mice were obtained (BALB/c− Hilltop Lab Animals, Inc., Scottdale, Pa.) and housed in Rutgers Laboratory Animal Services facility accredited by the Association for the Assessment and Accreditation of Laboratory and Care International (AAALAC). They were maintained on a 12-hour light/dark cycle and received laboratory chow and water ad libitum. Animals were housed three per cage and allowed to acclimatize at least 1-day prior to the studies. A day prior to the study, the mice were anesthesia with isoflurane (AErrane. Catalog #NDC 10019-773-40, Baxter, Deerfield, Ill.) and Veet (Reckitt Benckiser North America, Inc., Parsippany, N.J.) was applied on the clipped skin. Veet was removed 5 minutes post application and rats were washed with warm water and wiped with dry paper towels.

Preparation of Hydrogel Solution

The procedure for the preparation of phosphate buffer, preparation of polymer solution, preparation of cross-linker solution and preparation of hydrogel were used as set forth above in Example 1.

Subcutaneously Administration and In Situ Hydrogel Formation

The hydrogel solution (0.1 mL, polymer solution and crosslinker solution) prepared above was injected into mice subcutaneously using a 28 G needle attached to a 1 ml syringe. The solution started becoming more viscous and formed hydrogel in 1 min.

Hydrogel Degradation in Mice

After the hydrogel administration, size of the hydrogel was measured using vernier caliper. The size of the hydrogel was measured at different time points. Hydrogels prepared using degradable EMXL cross-linker was retained for 14 days.

EXAMPLE 34

GABAEMXL-Hydrogel Degradation Studies in Mouse

Animal

Mice were obtained (BALB/c− Hilltop Lab Animals, Inc., Scottdale, Pa.) and housed in Rutgers Laboratory Animal Services facility accredited by the Association for the Assessment and Accreditation of Laboratory and Care international (ANALAC). They were maintained on a 12-hour lightidark cycle and received laboratory chow and water ad libitum, Animals were housed three per cage and allowed to acclimatize at least 1-day prior to the studies. A day prior to the study, the mice were anesthesia with isoflurane (AErrane, Catalog #NDC 10019-773-40, Baxter, Deerfield, Ill.) and Veet (Reckitt Benckiser North America, Inc., Parsippany, N.J.) was applied on the clipped, skin. Veet was removed 5 minutes post application and rats were washed with warm water and wiped with dry paper towels.

Preparation of Hydrogel Solution

The procedure for the preparation of phosphate buffer, preparation of polymer solution, preparation of cross-linker solution and preparation of hydrogel were used as set forth above in Example 2.

Subcutaneously Administration and in situ Hydrogel Formation

The hydrogel solution (0.1 mL polymer solution and crosslinker solution) prepared above was injected into mice subcutaneously using a 28 G needle attached to a 1 ml syringe. The in situ solution started becoming more viscous and formed hydrogel in 1 min Hydrogel Degradation in Mice After the hydrogel administration, size of the hydrogel was measured using vernier caliper. The size of the hydrogel was measured at different time points. Hydrogels prepared using degradable EMXL cross-linker was retained for ~14 days.

ABBREVIATIONS

μL: Microliter
μm: Micron
—CONH—: Amide bonds
DAP: Polyoxyethylene bis(amine)
DCM: Dichloromethane
DIEA: N,N-Diisopropylethylamine
DIPC: Diisopropylcarbodiimide
DMF: N,N-dimethylformamide
DOX: Doxorubicin hydrochloride, an anthracycline drug used in cancer chemotherapy
DTT: DL-Dithiothreitol
EGF: Epidermal growth factor peptide
Eight-arm PEG-[SH]$_8$: Hexa-glycerine; octa-(thioethylene) poly(ethylene glycol) ether
FITC-Dextran: Fluorescein isothiocyanate-dextran
HBVS: 1.6-hexane-his-vinyl sulfone
HOBt: N-hydroxybenzotriazole
kDa: Kilo Daltons
min: Minutes
$Na_2CO_3$: Sodium carbonate
NHS: N-hydroxy succinimidyl ester (also called activated ester)
PB: Phosphate buffer
PBS: Phosphate buffered saline
PEG: Poly(ethylene glycol) polymer
PyBOP: Benzotriazol-1-yl-oxytripyrrolidinophosphonium hexafluorophosphate
RGDC: Argine-Glycine-Aspartic acid-Cysteine; RGD tripeptide motif is recognized by integrin receptors overexpressed on tumor cell surfaces
—S—: Thioether bond
SH: Thiol functional group
—S—S—: Disulfide bond
temp: Temperature

REFERENCES

The disclosures of all patent and non-patent literature cited in this application are hereby incorporated by reference in their entireties.

1. Bell, C. L.; Peppas, N. A. Poly(methacrylic acid-g-ethylene glycol) Hydrogels as pH Responsive Biomedical Materials. N. A. *Mater. Res. Soc. Symp. Proc.* 1994, 331, 199-204.
2. Peppas, N. A., *Hydrogels in Medicine and Pharmacy*; Volumes I, II, and III, CRC Press, Boca Raton, Fla., 1986.
3. Harris, J. M. *Poly(ethylene glycol) Chemistry. Biotechnical and Biomedical Applications*; Plenum Press, New York, 1992.
4. Zhao, X.; Harris, J. M. *Journal of Pharmaceutical Sciences,* 1998, 87, 11, 1450-1458.
5, Sawhney, A. S.; Pathak, C. P.; Hubbell, J. A. *Macromolecules* 1993, 26, 581-587.
6, Han, D. K.; Hubbell, J. A. *Macromolecules* 1996, 29, 5233-5235.
7. Sawhney, A. S.; Pathak, C. P.; van Renshurg, J. J.; Dunn, R. C.; Hubbell, J. A. *J. Biomed. Mater, Res.* 1994, 28, 831-838.
8. Llanos, G. R.; Sefton, M. V. *Macromolecules* 1991, 24, 6065-6072.
9. Llanos, G. R.; Sefton, M. V. *J. Biomed. Mater. Res.* 1993, 27, 1383-1391.
10. Andreopoulos, F. M.; Deible, C. R.; Stauffer. M. T.; Weber, S. G.; Wagner, W. R.; Beckman, E. J.; Russell, A. J. *J. Am. Chem. Soc.* 1996, 118, 6235-6240.
11. Saito, H.; Hoffman; A. S. *J. Bioact. Compat. Pol.,* 2007, 22, 589.
12. Li, C.; Yu, D. -F.; Newman, R. A.; Cabral, F.; Stephens, C. S.; Hunter, N.; Milas, L.; Wallace, S. *Cancer Res.* 1998, 58, 2404-2409.
13 Henne, W. A.; Doorneweerd, D. D.; Hilgenbrink, A. R.; Kularatne, S. A.; Low, P. S. *Bioorg. Med. Chem. Lett,* 2006, 16, 5350-5355.
14. Vasey, P. A. Kaye, S. B.; Morrison, R.; Twelves, C.; Wilson, P.; Duncan, R.; Thompson, A. H.; Muray, L. S.; Hilditch, T. E.; Muray, T.; Burtles, S.; Fraier, D.; Friegerio, E.; Cassidy J. Clin. *Cancer Res.* 1999, 5, 83-94.
15. Harris, J. M. Delivery of poly(ethylene glycol)-modified molecules from degradable hydrogel U.S. Pat. No. 6,258,351.
16. Andac, M.; Plieva, F. M.; Denizli, A. Galaev, I. Yu.; Mattiasson, B. *Macromol. Chem. Phys.* 2008, 209, 577-584.
17. Lin, C. C.; Metters, A. T. *Adv. Drug Deliv. Rev.,* 2006, 58, 1379-1408 and references therein.
18. Vervoort, L.; Rombaut, P.; Van den Mooter, G.; Augustijins, P.; Kinget, R. *Int. J. Pharm.* 1998, 172,137-145.
19, Masao, T.; Yoshimmi, K European Patent EP0838224, 1997.
20. (a) Lehninger, A. L.; *Biochemistry: The Molecular Basis of Cell Structure and Functions*, Worth Publishers, Inc., New York, 1975, 583, 807; (b) Chen, G.; Russell J. B. *J. Bacteriol.* 1989, 2981.
21. Deshmukh, M., Kutscher, H., Stein, S.; Sinko, P. *Chemistry & Biodiversity.* 2009, 6, 527-539.
22. King, B. L.; Love, S. M. *Breast Cancer Res* 2006, 8, 1-10.
23. Qiu. B.; Stefanos. S. Ma. S.; Lalloo. A.; Perry. B. Leibowitz. M. J.; Sinko. P. J.; Stein, S. *Biomaterials,* 2003, 24, 11-18.
24. Udenfriend, S., Stein, S. S.; Peter Böhlen, P.; Dairman, W.; Leimgruber, W.; Weigele. M. *Science,* 1972, 178, 4063, 871-872.

What claimed is:

1. A pharmaceutical formulation capable of forming a biodegradable hydrogel in situ to provide timed release of an active agent comprising:
   (1) a therapeutically effective amount of one or more active agents,
   (2) a hydrophilic agent that is a polyethylene glycol polymer or copolymer comprising a plurality of cross-linking functional groups, and
   (3) a multifunctional polyethylene glycol cross-linker comprising a plurality of cross-linking functional groups co-reactive with said cross-linking functional groups on said hydrophilic agent, which forms a hydrogel in situ by interaction between said co-reactive functional groups on the cross-linker and said co-reactive functional groups on the hydrophilic agent, wherein:
   one of said hydrophilic agent and said cross-linker comprise a polyethylene glycol with up to eight degradable cross-linking functional group segments independently comprising the structure:

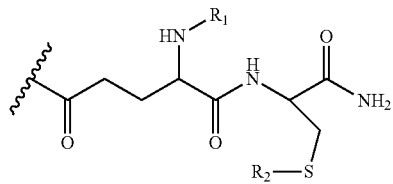

wherein $R_1$ is H, an amino acid selected from the group consisting of GABA (gamma-amino butyric acid), AHA (6-aminohexanoic acid) and AOA (8-aminooctanoic acid), or an amino acid dimer, each member of which is independently selected from the group consisting of GABA, AHA and AOA; and $R_2$ is a functional group that reacts with a functional group on the other of said hydrophilic agent and said cross-linker to form said hydrogel; and
   one of said hydrophilic agent and said cross-linker further comprises a pendant degradable segment comprising a glutamic acid moiety having the structure:

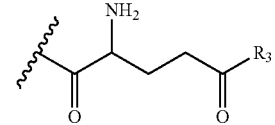

wherein $R_3$ is an active agent comprising a free amino group bonded to the-γ-carboxylic group of said glutamic acid moiety through an amide bond, and the free α-amino group of said glutamic acid moiety provides timed cleavage by reacting with the γ-carboxylic group, resulting in cleavage of the γ-amide bond and formation of a five member cyclic ring, releasing the active agent.

2. The formulation of claim 1, wherein the hydrophilic agent is a multi-arm thiol-containing PEG, and the crosslinker is a multifunctional PEG cross-linker containing thiol-reactive function groups.

3. The formulation of claim 2, wherein the thiol-reactive function groups are selected from the group consisting of a vinylsulfone, a maleimide and combinations thereof.

4. The formulation of claim 1, wherein the cross-linker contains thiol groups, and the hydrophilic agent is a multi-arm PEG containing thiol-reactive functional groups.

5. The formulation of claim 4, wherein the thiol-reactive functional groups are selected from the group consisting of a vinylsulfone, a maleimide and combinations thereof.

6. The formulation of claim 1, wherein the concentration of the hydrophilic polymer or copolymer is from about 1 to about 20% (w/v).

7. The formulation of claim 1, wherein the concentration of the cross-linker is from about 1 to about 15% (w/v).

8. The formulation of claim 1, wherein the ratio of the polymer or copolymer to the cross-linker is from about 0.05:10 to about 10:0.05.

9. The formulation of claim 1, wherein the polyethylene glycol is a linear or multi-arm having from 2 to 8 arms.

10. The formulation of claim 1, wherein the polyethylene glycol contains multiple thiol groups and has a molecular weight from about 1000-100,000 Da.

11. The formulation of claim 1, wherein the cross-linker is selected from the group consisting of EMXL ($CONH_2$-Cys(VS)-Glu($NH_2$)-PEG-Glu($NH_2$)-Cys(VS)—$CONH_2$), GABA-EMXL(CONH$_2$-Cys(VS)-Glu(GABA-NH$_2$)-PEG-Glu(GABA-NH$_2$)-Cys(VS—)—CONH$_2$), and combinations thereof.

12. The formulation of claim 1, wherein R$_2$ is derived from an agent selected from the group consisting of BM[PEO]$_3$ (1,8-bis-maleimidotriethyleneglycol), BM[PEO]$_4$ (1,11-bis-maleimidotriethyleneglycol), BMH (bis-maleimidohexane), BMOE (bis-baleimidoethane) and combinations thereof.

13. The formulation of claim 1, wherein the cross-linker is selected from the group consisting of rEMXL, dithiothreitol, polycysteines, PEG-dithiol, a 4-arm thiol and combinations thereof.

14. The formulation of claim 1, wherein the active agent is present in a concentration of about 0.1 to about 12% (w/v), and is passively entrapped in the hydrogel.

15. The formulation of claim 1, wherein the active agent is bonded to the hydrogel, and is present in a concentration of about 1 to about 10% (w/v).

16. The formulation of claim 1, wherein the active agent is selected from the group consisting of: anti-inflammatory drugs, NSAID analogs, NSAID-ache (NSAID-acetylcholinesterase complexes, steroidal anti-inflammatory drugs, anticancer drugs, HIV protease inhibitors, monoclonal antibodies, imaging agents, and combinations thereof.

17. The formulation of claim 1, wherein the active agent is selected from the group consisting of: sancycline, olvanil, retro-olvanil, doxorubicin, saquinavir mesylate, amprenavir, indinavir, tipranavir, darunavir, a coloring dye, rhodamine, Alexa, and combinations thereof.

18. The formulation of claim 1, wherein the active agent is modified with a targeting moiety selected from the group consisting of: an RGD peptide, EGF peptide, DV3 (LGASWHRPDKC) (SEQ ID NO:1) peptide, a LYP peptide (CGNKRTRGC) (SEQ ID NO:2), membrane-binding domain of IGFBP3 (QCRPSKGRKRGFCW) (SEQ ID NO:3), fMLF, mannose, transferrin ligand, and monoclonal antibodies.

19. The formulation of claim 1, wherein the active agent is doxorubicin which is modified with a targeting moiety selected from the group consisting of: Leu-Gly, Glu(Leu-Gly)2 (SEQ ID NO:4), Arg-Gly-Asp-Cys (SEQ ID NO:5), Gly-Arg-Gly-Asp-Ser (SEQ ID NO:6), Gly-Arg-Gly-Asp-Ser-Pro (SEQ ID NO:7), cyclic Arg-Gly-Asp-Tyr-Lys (SEQ ID NO:8), any peptide with Arg-Gly-Asp, and combinations thereof.

* * * * *